United States Patent
Clapp et al.

(10) Patent No.: US 8,933,082 B2
(45) Date of Patent: Jan. 13, 2015

(54) MATERIALS AND METHODS FOR SUPPRESSING AND/OR TREATING NEUROFIBROMA AND RELATED TUMORS

(71) Applicants: D Wade Clapp, Indianapolis, IN (US); David Ingram, Indianapolis, IN (US); Feng-Chun Yang, Carmel, IN (US)

(72) Inventors: D Wade Clapp, Indianapolis, IN (US); David Ingram, Indianapolis, IN (US); Feng-Chun Yang, Carmel, IN (US)

(73) Assignee: Indiana University Research and Technology Corp., Indianapolis, IN (US)

( * ) Notice: Subject to any disclaimer, the term of this patent is extended or adjusted under 35 U.S.C. 154(b) by 0 days.

(21) Appl. No.: 14/032,994

(22) Filed: Sep. 20, 2013

(65) Prior Publication Data
US 2014/0121214 A1  May 1, 2014

Related U.S. Application Data

(62) Division of application No. 12/996,891, filed as application No. PCT/US2009/048554 on Jun. 25, 2009, now abandoned.

(60) Provisional application No. 61/076,185, filed on Jun. 27, 2008, provisional application No. 61/103,650, filed on Oct. 8, 2008.

(51) Int. Cl.
*A61K 31/4965* (2006.01)

(52) U.S. Cl.
USPC ..................... 514/255.05; 514/275

(58) Field of Classification Search
USPC ............................. 514/255.05, 275
See application file for complete search history.

(56) References Cited

U.S. PATENT DOCUMENTS

| | | | |
|---|---|---|---|
| 5,521,184 A | 5/1996 | Zimmermann | |
| 6,894,051 B1 | 5/2005 | Zimmermann | |
| 2004/0077661 A1* | 4/2004 | Arbiser | 514/255.05 |
| 2005/0267125 A1 | 12/2005 | Luftensteiner et al. | |
| 2009/0203709 A1 | 8/2009 | Steinberg et al. | |

FOREIGN PATENT DOCUMENTS

WO WO2007/065898 6/2007

OTHER PUBLICATIONS

Yang et al., Human Molecular Genetics, 2006, 15(16): 2421-2437.*
International Searching Authority, Declaration of Non-Establishment of International Search Report for PCT/US2009/048554, issued Jan. 2010.
International Searching Authority, Written Opinion for PCT/US2009/048554, issued Jan. 2010.
International Searching Authority, International Preliminary Report on Patentability for PCT/US2009/048554, issued Jan. 2011.
Yang, et al., Human Molecular Genetics, 2006, 15(16): 2421-2437.
English Translation of Dermal and Venerologic Diseases. Guidline for the Medics, Edited by Academician Yu K. Skripkin, Provessor V.N. Mordovtsev, in two Volumes, vol. 2, Second edition, revised and enlarged pp. 730-737, Moscow, "Medicine" 1999 (relevant parts only).
Van Westen et al. CAS: 157:454563, 2011.
Han Sang Hoon et al., "Malignant gastrointestinal stromal tumor in a patient with neurofibromatosis type 1." The Korean Journal of Internal Medicine, Mar. 2007, vol. 22, No. 1, pp. 21-23.
Aoki Mikiko et al., "Imatinib mesylate inhibits cell invasion of malignant peripheral nerve sheath tumor induced by platelet-derived growth factor-BB" Laboratory Investigation, Nature Publishing Group, US vol. 87, No. 8, Jan. 2007, pp. 767-779.
Holtkamp, Nikola, et al., "Mutation and Expression of PDGFRA and KIT in malignant peripheral nerve sheath tumors, and its implications for imatinib sensitivity," Cacinogenesis, Oxford University Press, GB, vol. 27, No. 3, Mar. 2006, pp. 664-671.
Yang, Feng-Chun et al, "Nfl-Depednetn Tumors Require a Microenvironment Containing Nfl (+/−) and c-kit-Dependent Bone Marrow" Cell vol. 135, No. 3, Oct. 2008, pp. 437-448.
European Patent Office, Supplementary European Search Report for EP 09 77 0980, dated May 13, 2011, 6 pages.

* cited by examiner

*Primary Examiner* — Rei-tsang Shiao
(74) *Attorney, Agent, or Firm* — Faegre Baker Daniels LLP

(57) ABSTRACT

Germline mutations in the NF1 tumor suppressor gene cause Von Recklinghausen's neurofibromatosis type 1 (NF1), a common genetic disorder of the nervous system characterized by plexiform neurofibroma development. Using adoptive transfer of hematopoietic cells, we establish that NF1 heterozygosity of bone marrow derived cells in the tumor microenvironment is sufficient to allow neurofibroma progression in the context of Schwann cell nullizygosity. Further, genetic or pharmacologic attenuation of the c-kit signaling pathway in hematopoietic cells greatly diminishes neurofibroma initiation and progression. These studies identify haploinsufficient hematopoietic cells and the c-kit receptor as therapeutic targets for preventing plexiform neurofibromas and implicate mast cells as critical mediators of tumor initiation. Administering therapeutically effective doses of a tyrosine kinase inhibitor such as the compound imatinib mesylate to a patient in need thereof to treat tumors in a human patient afflicted with plexiform neurofibroma.

8 Claims, 32 Drawing Sheets

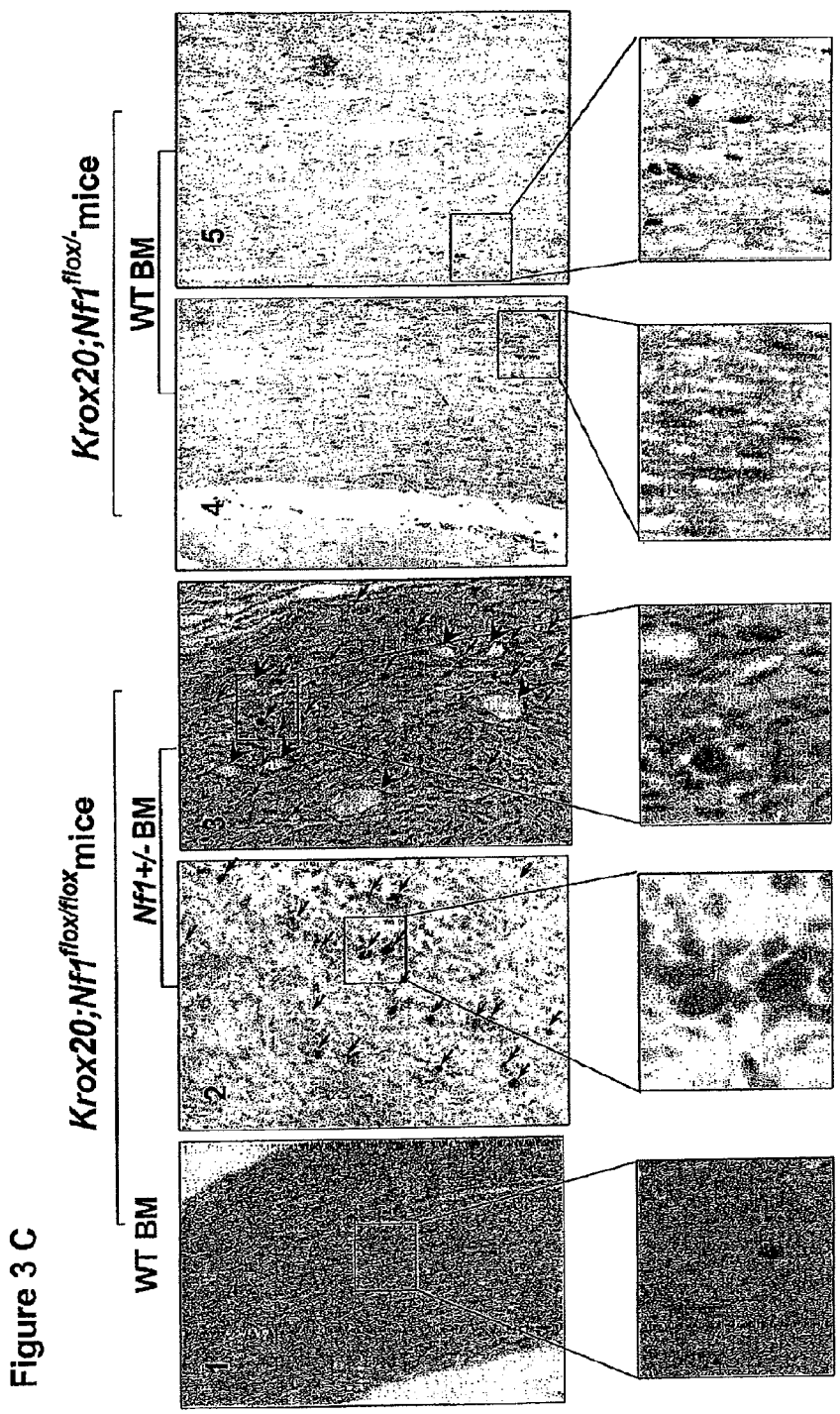

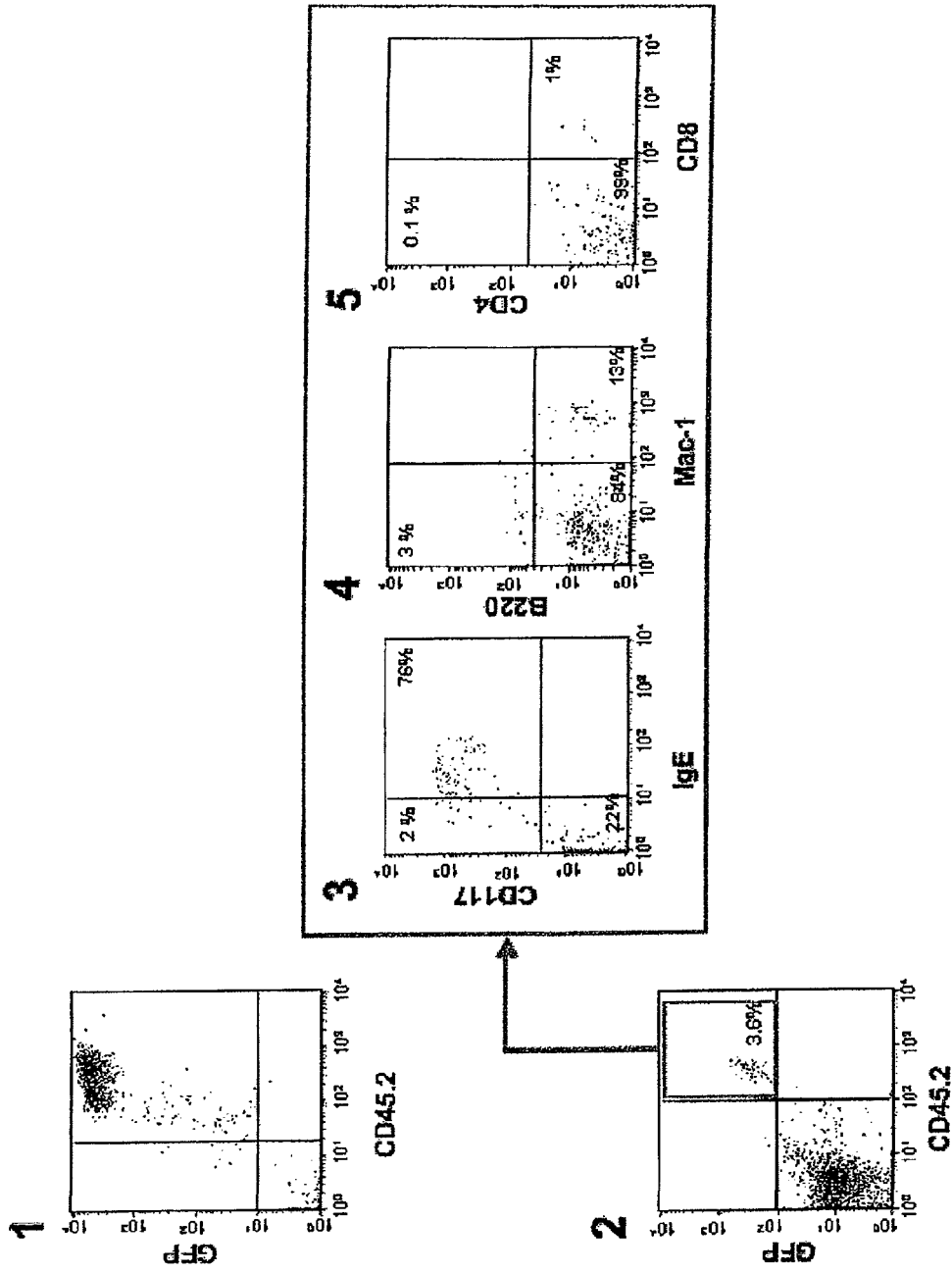

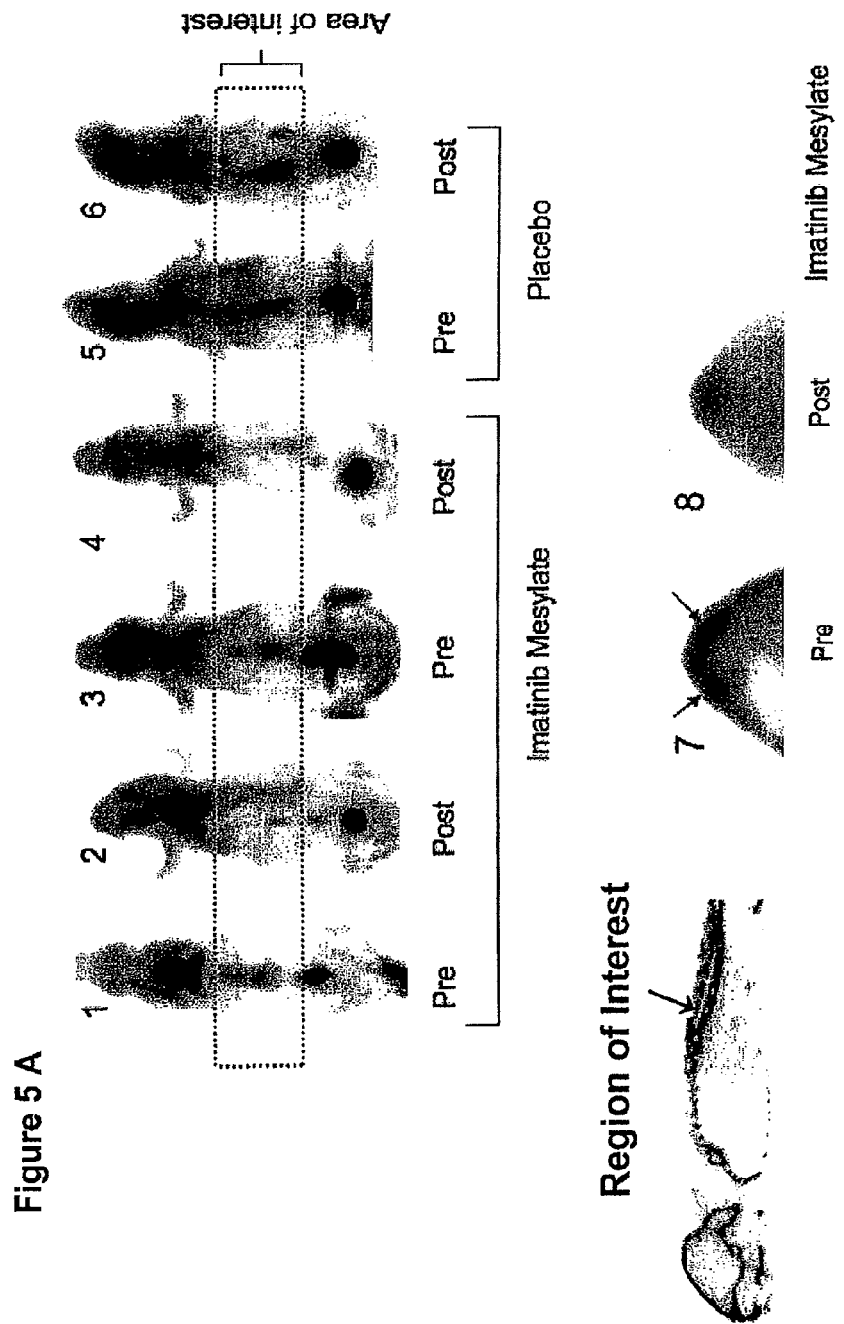

Three months treatment with imatinib mesylate

Before

Toludine blue

MATERIALS AND METHODS FOR SUPPRESSING AND/OR TREATING NEUROFIBROMA AND RELATED TUMORS

PRIORITY CLAIM

This application is a divisional of U.S. patent application Ser. No. 12/996,891 filed Mar. 24, 2011, which is a National Stage filing of International Application Serial No. PCT/US2009/048554, filed Jun. 25, 2009 and designating the United States, which claims priority to U.S. Provisional Application Ser. Nos. 61/076,185 filed Jun. 27, 2008 and 61/103,650 filed Oct. 8, 2008, the disclosures of which are expressly incorporated herein by reference.

STATEMENT OF GOVERNMENTAL RIGHTS

This invention was made with government support under NS052606 awarded by the National Institutes of Health and W81XWH-05-1-0185 awarded by the Department of Defense. The U.S. Government has certain rights in the invention.

FIELD OF THE INVENTION

Various aspects and embodiments disclosed herein relate generally to the modeling, treatment, prevention and diagnosis of diseases characterized by the formation of tumors, for example, neurofibroma.

BACKGROUND

Mutations in the NF1 tumor suppressor gene cause neurofibromatosis type 1 (NF1), a common, widely distributed human genetic disorder that affects approximately 250,000 patients in the US, Europe, and Japan alone. The NF1 gene encodes neurofibromin, a 320 kilodalton protein that functions, at least in part, as a GTPase activating protein (GAP) for p21ras. Neurofibromin is highly conserved among vertebrate species and has high homology with its counterparts, yeast and Drosophila.

Individuals with NF1 exhibit a wide range of malignant and nonmalignant manifestations, including plexiform neurofibromas that collectively affect 25-40% of NF1 patients; these neurofibromas are a major source of life long morbidity and mortality. Given the negative impact that this condition has on people with this mutation and the dearth of effective treatments for this and related condition there is a pressing need for additional treatments for this condition. Various aspects and embodiments disclosed herein address this need.

SUMMARY OF THE INVENTION

Some embodiments include methods of treating a patient having a form of neurofibromatosis, for example, plexiform neurofibroma, comprising the steps of: providing at least one therapeutically effective dose of a compound according to Formula 1:

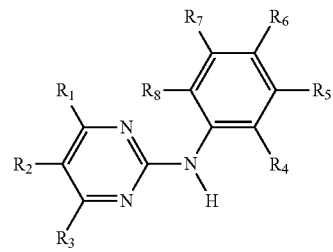

wherein, $R_1$ is 4-pyrazinyl; 1-methyl-1H-pyrrolyl; amino- or amino-lower alkyl-substituted phenyl, wherein the amino group in each case is free, alkylated or acylated; 1H-indolyl or 1H-imidazolyl bonded at a five-membered ring carbon atom; or unsubstituted or lower alkyl-substituted pyridyl bonded at a ring carbon atom and unsubstituted or substituted at the nitrogen atom by oxygen; $R_2$ and $R_3$ are each independently of the other hydrogen or lower alkyl; one or two of the radicals $R_4$, $R_5$, $R_6$, $R_7$ and $R_8$ are each nitro, fluoro-substituted lower alkoxy or a radical of formula II $$—N(R_9)—C(=X)—(Y)_n—R_{10} \qquad (II),$$

wherein, $R_9$ is hydrogen or lower alkyl, X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms, or an aromatic, aromatic-aliphatic, cycloaliphatic, cycloaliphatic-aliphatic, heterocyclic or heterocyclic-aliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterified hydroxy, free, alkylated or acylated amino or free or esterified carboxy, or of a salt of such a compound having at least one salt-forming group.

In some embodiments the compound is a pharmaceutically acceptable salt of Formula 1, in some embodiment the pharmaceutically acceptable salt of Formula 1 is a mesylate salt.

Some other embodiments further include the step of; diagnosing a patent with plexiform neurofibroma or a similar condition. While still other embodiments include the step of identifying a patent at risk for developing plexiform neurofibroma or a similar condition.

In some embodiment the therapeutically effective dose of the compound according to Formula 1, is on the order of between about 200 mg to about 500 mg and the dose of the compound is administered to at patient at least once per day. In still other embodiments the therapeutically effective dose of the compound according to Formula 1, is on the order of between about 350 mg to about 450 mg and the dose of the compound is administered to at patient at least once per day. In some embodiment a patient is treated twice dialing with a therapeutically effective dose of the compound according to Formula 1, of about 400 mg.

Some embodiments include treating a patent having a form of neurofibromatosis, for example, plexiform neurofibroma, comprising the steps of: providing at least one therapeutically effective dose of a compound according to Formula 2:

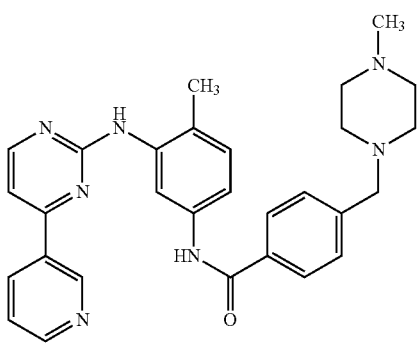

(2)

Still other embodiments include a method of treating a patent having a form of neurofibromatosis, for example, plexiform neurofibroma, comprising the steps of: providing at least one therapeutically effective dose of a compound according to Formula 3:

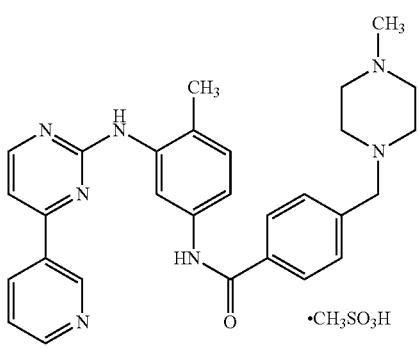

(3)

Still other embodiments include the use of at least one compound according to Formulas (1), (2) or (3) or a pharmaceutically acceptable salt thereof for the preparation of a medicament for treating a patient having a form of neurofibromatosis, for example, plexiform neurofibroma.

BRIEF DESCRIPTION OF THE FIGURES

The above-mentioned aspects of the present disclosure and the manner of obtaining them will become more apparent and aspects thereof will be better understood by reference to the following description of the embodiments of the disclosure, taken in conjunction with the accompanying drawings, figures, schemes, formula and the like, wherein.

Corresponding reference numerals are used to indicate corresponding parts throughout the several views.

DETAILED DESCRIPTION

Figure 1A:
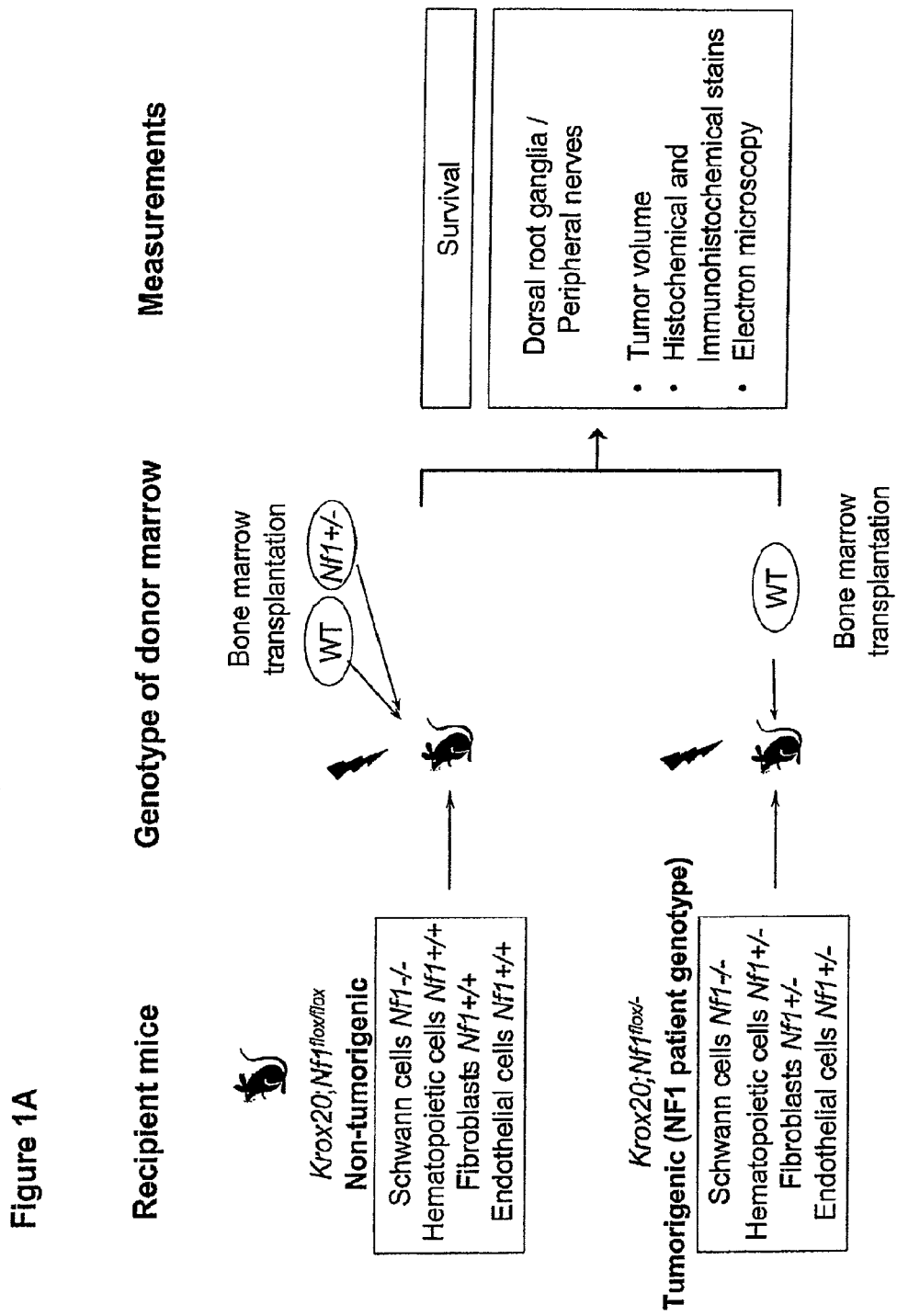
FIG. 1A. A schematic diagram of a strategy for examining the role of the hematopoietic microenvironment.

The embodiments of the presented and/or described below are not intended to be exhaustive or to limit the precise forms disclosed in the following detailed description. Rather, the embodiments are chosen and described so that others skilled in the art may appreciate and understand the principles and practices of various aspects and embodiments discussed herein.

Animals models for various diseases have proven to be very effective tools for developing an understanding of the modeled disease and perhaps as importantly, for developing and testing new materials and/or methods for diagnosing, treating and/or preventing the modeled disease. Murine models that purport to enable the dissection of cell autonomous and non-cell autonomous contributions to tumor development have gained considerable prominence. Rigorous scrutiny must be exercised when extrapolating mouse tumor model to humans and the significance of such experimental strategies can only be appreciated in the context of a clear and verifiable physiological relevance to the human disease state.

Accordingly, a cardinal principle in mouse modeling of human cancer requires that mutations of relevant molecular pathways be developed in the same tissues as the human tumors. Furthermore, the mouse tumors used to model the human disease should recapitulate the human phenotype in a credible series of cellular and molecular outcomes. Provided, adequate care is taken when designing the experiment and interpreting the results, mouse models have been successfully used to study tumor development in humans. For example, genetic modeling is especially fruitful when human tumors are the consequence of a genetically inheritable trait that can be reduced to a single gene mutation such as in the case of Von Recklinghausens's Neurofibromatosis. Accordingly, some aspects of the instant invention teach a mouse model suitable for minimizing some forms of neurofibroma formation in humans. Perhaps the best evidence that an animal model for a given disease has efficacy in developing treatments for the same or similar diseases in humans is to demonstrate that unlike many animal models for human diseases treatments devised on the basis of the particular animal model are shown to have efficacy in the treatment of human patients.

Development of a Mouse Model for Neurofibromatoris

Von Recklinghausen's Neurofibromatosis is a single gene disorder. In the vast majority of cases it is manifested by a germline mutation and complete somatic heterozygosity followed by a rare loss of heterozygosity in cell types that engender the stereotypic manifestations of this disease. Almost invariably in this disorder, tumors develop in the peripheral nervous system of the affected patient. Human tissue studies suggest a critical role for Schwann cells but these studies suffer from relying on a posteriori information to infer a preceding event. A conditional Nf1 knockout mouse model that permits tissue specific deletion of Nf1 has shed light on this process. In the physiologically relevant context of global heterozygosity, these studies reveals that the genetic bottleneck for plexiform neurofibroma formation likely lies in the loss of Nf1 heterozygosity in the embryonic Schwann cell lineage. The histopathological analysis of these tumors is virtually indistinguishable from native human tumors.

The power of mouse genetics reveals a critical role for a microenvironment that could, in distinct genetic configurations, be either tumor permissive or tumor resistant. The data indicate that Nf1 heterozygosity outside the Schwann cell lineage is required for tumor formation. For example, mast cell infiltration into peripheral nerves appears in these mice months prior to the appearance of tumors, but not in the non tumorigenic Nf1 wild type ($^{flox/flox}$) genotype. Mast cells have been observed in human neurofibromas, although in the absence of a mouse model, examination of a functional role in tumor development or maintenance could not be directly studied. It is interesting to note that the requirement for Nf1 haploinsufficiency has been replicated with additional Cre transgenes that target the neural crest Schwann cell lineage including periostin-Cre, P0-Cre and tamoxifen inducible PLP-Cre. These observations further validate the need for Nf1 heterozygosity outside of the Schwann cell lineage. Data gathered using tissue specific Cre transgenes do not rule-out the possibility that tumors may develop in a wild type environment under contrived experimental conditions. Indeed, when we utilize neural crest specific Cre drivers that have early, widespread, and robust expression, we observe hyperplasia of the peripheral nerves even in $^{flox/flox}$ mice, although less so than in the $^{flox/-}$ mice.

Results disclosed herein illustrate that the latter models depart from the physiological situation in humans with NF1 in which LOH is such a rare stochastic event that a nullizygous embryonic Schwann cell precursor arising in isolation is at a relative disadvantage in a microenvironment to develop into a tumor. These mouse models indicate that an isolated nullizygous pocket of cells gain a significant selective advantage by apparent synergy with recruited heterozygous mast cells. One interpretation of these results, consistent with the data, is that hyperplasia in robust Cre mediated recombination models reflects a nonphysiologic widespread loss of Nf1, not only in Schwann cells but also an additional Nf1 loss in additional lineages that may overcome the barriers of isolated LOH.

Neurofibromas form in association with peripheral nerves and are composed of Schwann cells, endothelial cells, fibroblasts, degranulating inflammatory mast cells, and pericytes/ vascular smooth muscle cells (VSMCs) and contain large collagen deposits. An Nf1 conditional knockout mouse model confirms retrospective studies from human tumors, demonstrating that Nf1 loss of heterozygosity (LOH) in the Schwann cell lineage appears to be necessary but not sufficient to elicit neurofibromas. As reported, tumor progression requires complex interactions between Schwann cells and Nf1 haploinsufficient cell lineages in the tumor microenvironment. Thus, in a Nf1 WT background, Nf1 nullizygosity in Schwann cells may be necessary but not necessarily sufficient to cause tumor formation. One reported characteristic of tumor forming heterozygous mice is the appearance of mast cells in peripheral nerves well in advance of tumor development. Additionally, in vitro experiments mixing Schwann cell conditioned media and mast cells demonstrate a hypersensitivity of Nf1 heterozygous mast cells to conditioned media from nullizygous Schwann cells. With out wishing to be bound by any specific theory we hypothesized a model for the formation of those types of tumors, comprising Nf1 heterozygous mast cell infiltration of preneoplastic peripheral nerves and association with Nf1 nullizygous Schwann cells contributing to tumor development.

The finding that adoptive transfer of heterozygous Nf1$^{+/-}$ derived bone marrow is sufficient to cooperate with the resident nullizygous Schwann cell lineage specific ablation to induce tumor formation, in an otherwise WT environment, suggests that the requirement for haploinsufficiency resides in bone marrow derived cells but not the other cell types found in these tumors. In addition, the genetic requirement for c-Kit signaling in the donor bone marrow and the infiltration of donor heterozygous mast cells into the incipient peripheral nerve tumors strongly supports the hypothesis that this constitutes a causal interaction.

The c-Kit receptor has a central role in mast cell development and function. Schwann cells and fibroblasts, two principal components of neurofibromas, secrete kit-ligand in response to many different stimuli. For example, elevated kit-ligand mRNA transcripts have been reported in neurofibroma tissue and it has been reported that NF1 patients have elevated levels of kit ligand in their serum. In preclinical trials Imatinib mesylate, an FDA-approved pharmacological agent was thought to act by inhibiting several tyrosine kinases including c-Kit.

When tested for efficacy against neurofibroma in a mouse model for the disease, Imatinib mesylate exhibited an unexpected efficacy. Administering therapeutically effective doses of the compound has a dramatic effect on the reversal of neurofibroma pathology. Treatment with imatinib resulted in the disappearance of mast cells from the peripheral nerves in animals treated with this compound. In addition to extending in vitro studies that demonstrate c-Kit mediated interactions between NF1 Schwann cells and heterozygous mast cells, the in vivo studies identify a persisting requirement for imatinib mesylate responsive tumor maintenance.

The role of inflammation and mast cells in tumor development is an active area of research. Mast cells release mediators of inflammation including histamine, serotonin, proteoglycans, and leukotrienes subsequent to activation of the high affinity IgE receptor (FcεRI) and the c-kit receptor. Furthermore, mast cells reportedly release VEGF, an angiogenic factor that is also a potent proliferative, survival, and chemotactic factor for Schwann cells. VEGF has also been linked to an angiogenic switch in tumor formation. Finally, mast cells also release PDGF-β, a growth factor that promotes pericyte and fibroblast proliferation; and TGF-β, a growth factor that promotes fibroblast proliferation and collagen synthesis.

Imatinib Mesylate and the Tumor Microenvironment.

An important question in the context of neurofibromas is how do mast cells cooperate with Schwann cells to elicit tumor formation? Data presented herein indicates that other cell types in the tumor needn't necessarily be heterozygous. However, it is too early to assert whether the infiltrating Nf1 heterozygous mast cell primarily acts reciprocally on the nullizygous Schwann cells to promote tumor formation or alternatively whether indirect interaction with local stroma and additional cell types also present in these tumors are requisite intermediaries for tumor induction. A better understanding of additional paracrine interactions within neurofibromas and how they may influence tumor formation and maintenance await additional study.

In addition, genetic results reported herein and in previous in vitro studies demonstrated that imatinib mesylate inhibits multiple Nf1$^{+/-}$ pericyte, and fibroblast tumor promoting functions. Again, the absence of requirement for heterozygosity in these additional tumor cells, do not rule out the possibility that the ability of imatinib mesylate to cause the regression of tumors may not be exclusively caused by its inhibitory activity on mast cells. The following hypothesis is presented by way of illustration and not limitation the fact that treatment with the compounds such as imatinib mesylate reduces tumors is an aspect of the invention and in no way dependent on the veracity of any given theory or explanation proffered in an attempt to explain this result. Imatinib mesylate and compounds of the same or similar families of compounds may fortuitously inhibit additional and/or other potentially critical tumor promoting activities in other tumor cell types. For instance, in addition to inhibiting c-Kit in mast cells, imatinib mesylate may decrease angiogenesis via PDGFR and reduce fibrosis/collagen production via c-Abl. Additional investigation may be required to resolve these critical and fascinating scenarios, in the interim, one observation is that an effective dose of this compound causes tumor regression in the mouse model for neurofibromas and in human patients affiliated with conditions such as plexiform neurofibromas.

Pharmacologic Inhibition of c-Kit Reduces Tumor Size and Metabolic Activity.

Compounds that may be used to practice the present invention include compounds of Formula 1:

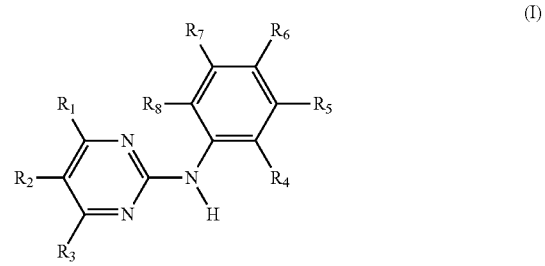

wherein; $R_1$ is 4-pyrazinyl; 1-methyl-1H-pyrrolyl; amino- or amino-lower alkyl-substituted phenyl, wherein the amino group in each case is free, alkylated or acylated; 1H-indolyl or 1H-imidazolyl bonded at a five-membered ring carbon atom; or unsubstituted or lower alkyl-substituted pyridyl bonded at a ring carbon atom and unsubstituted or substituted at the nitrogen atom by oxygen; $R_2$ and $R_3$ are each independently of the other hydrogen or lower alkyl; one or two of the radicals $R_4$, $R_5$, $R_6$, $R_7$ and $R_9$ are each nitro, fluoro-substituted lower alkoxy or a radical of formula II $$-N(R_9)-C(=X)-(Y)_n-R_{10} \qquad (II),$$

wherein, $R_9$ is hydrogen or lower alkyl, X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms, or an aromatic, aromatic-aliphatic, cycloaliphatic, cycloaliphatic-aliphatic, heterocyclic or heterocyclic-aliphatic radical, and the remaining radicals $R_4$, $R_5$, $R_6$, $R_7$ and $R_9$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterified hydroxy, free, alkylated or acylated amino or free or esterified carboxy, or of a salt of such a compound having at least one salt-forming group.

The compounds of Formula 1 are generically and specifically disclosed in the patent applications U.S. Pat. No. 5,521,184, in particular in the compound claims and the final products of the working examples, the subject-matter of which is herein incorporated by reference in its entirety. In the above definition of the compound of Formula 1 the radicals and symbols have the meanings as provided in U.S. Pat. No. 5,521,184, which is incorporated herein in its entirety.

For the purpose of the present invention, Imatinib may be applied in the form of its mono-mesylate salt. Imatinib monomesylate can be prepared in accordance with the processes disclosed in U.S. Pat. No. 6,894,051, which is herein incorporated by reference in its entirety. Comprised are likewise the corresponding polymorphs, e.g. crystal modifications, which are disclosed therein.

In adult patients a daily dose of between about 200 and about 800 mg, e.g. 400 mg, of the mono-mesylate salt of Imatinib is administered orally. Imatinib mono-mesylate can be administered in dosage forms as described in U.S. Pat. No. 5,521,184, U.S. Pat. No. 6,894,051, US 2005/0267125 or WO2006/121941, all of which are incorporated herein in their entirety as if each were separately incorporated. For additional discussion of these compounds please see, for example, U.S. patent application Ser. No. 11/815,046 now U.S. publication No 2008/00114001 A1 published on May 15, 2008, which is incorporated herein by reference in its entirety.

One especially useful compound for treatment of disease that are thought to involve tyrosine kinase activity is the compound imatinib mesylate (4-(4-methylpiperazin-1-ylmethyl)-N-[4-methyl-3-(4-(pyridin-3-yl)pyrimidin-2-ylamino)phenyl]-benzamide) Imatinib can, e.g., be prepared in accordance with the processes disclosed in WO03/066613. One pharmaceutically acceptable salt of the compound is imatinib mesylate shown in Formula 3 as follows:

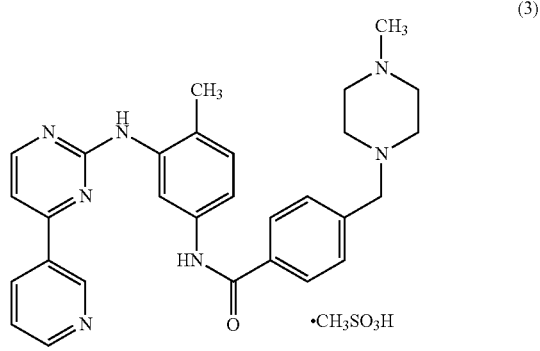

(3)

Imatinib mesylate is a potent inhibitor of the c-Kit, PDGF-BB, and c-abl tyrosine kinases. This compound is marketing in under the trademark protected name Gleevec. It has been approved in the United States for the treatment of patents with Kit-expressing (CD 117+). According to the National Guideline Clearinghouse (www.guidline.gov) the initial recommended dose level in adult human patients in 400 mg administered twice daily. The actual therapeutically effective dosage is patient specific and to be determined by the prescribing physician based on various factors including the patients weight, age, gender, age, overall health and responsiveness to the drug.

One limitation of the mouse model is the animal's short lifespan, given this one cannot predict on the basis of mouse studies how long-lived tumors might be expected to respond. However, these results with the mouse model strongly suggest that treatment with these compounds can and will have a beneficial effect on humans affected with some tumors. Additional support for this hypothesis comes from the unexpectedly good result when obtained when treatment of a human patient with imatinib mesylate successfully reduced the size of the tumor in the human patient.

By way of explanation and not limitation, the following discussion is proffered. Theories concerning the cellular and molecular mechanisms that underlie the development of idiopathic cancer have undergone significant evolution in recent years. The original notions that cell autonomous events convey a single cell to overcome its normal regulation leading to development of malignant disease, and furthermore the identity of the cell type of tumor origin, are presently under concerted reinvestigation. It is increasingly clear that while a series of genetic and epigenetic events in a single cell commence the trajectory toward a malignant phenotype, most forms of cancer include a co-option of a permissive microenvironment that allows and even promotes the tumorigenic state which, in accordance with this hypothesis, a resistant environment would essentially preclude the possibility of tumor formation. Among identified non-cell autonomous contributors to a co-opted permissive process of tumor formation are neo-angiogenesis, participation of the local stroma, and inflammation among other cell types. The understanding of the precise order of paracrine interactions, the relative importance, and the molecular basis of the nontumorigenic environment interaction, remains in infancy. However, the therapeutic uses of the compounds disclosed herein are in no way limited by any of the hypothesized modes of action or proposed molecular etiologies of the various diseases or condition that can adventurously treated or controlled using the materials and/or methods described herein.

These data are consistent with a role for bone marrow derived cells in plexiform neurofibroma formation. These data also indicates that pharmacologic and genetic inhibition of the c-kit receptor may prevent or at least delay plexiform neurofibroma formation in Nf1 mice. These results indicate that Nf1 haploinsufficiency of bone marrow derived cells and in particular those dependent on activation of the c-kit receptor is required in the tumor microenvironment to allow neurofibroma progression. The data implicate mast cells as active participants in tumor formation and identify novel therapeutic targets for human phase 1-2 clinical trials.

The instant disclosure provides an example of a physiologically relevant mouse model of a human cancer that provides concrete insights into complex interactions between a tumor cell of origin and the microenvironment. While, investigations using the mouse as a model for the human disease suggests a potential therapeutic approach for treating heretofore untreatable tumor by targeting the microenvironment for tumor formation rather than the tumorigenic cell. Because of the considerable cellular and physiological differences between human and mice, the efficacy of using compound such as imatinib mesylate to treat neurofibroma in humans can only be "proved" by successfully treating humans with the compound. At least in part because humans are generally more long lived than mice, the ability of imatinib mesylate to treat humans with conditions such as neurofibroma, unlike the situation with the use of this compound to treat chronic myelogenous leukemia, may lead to the development of drug resistance. In CML imatinib mesylate is thought to act directly on the leukemic cell and aimed at a mutated constitutively active tyrosine kinase oncoprotein (Bcr-abl). The Bcr-abl oncogene can develop drug resistance through the acquisition of second site mutations. In contrast, it is likely that the principal if not exclusive activity of anti-c-kit agents such as imatinib mesylate on neurofibromas is on non-tumor cell acting, for example, on WT proteins for which there may not be a ready route for the selection for drug resistance.

We have identified compounds that in vitro have as much as tenfold higher inhibitory activity on Nf1 heterozygous mast cells than does imatinib mesylate (unpublished results). A very small number of cases have been reported in which patients have both Von Recklinghausens's Neurofibromatosis and piebaldism. These studies inferred that piebaldism resulted from hypomorphic mutations of the c-Kit receptor. These patients were reported to lack neurofibromas. Another plausible explanation for the abstentions is that these individuals were deficient in mast cells. Accordingly, these reports may provide confirmation of the importance of c-Kit and mast cells in neurofibroma formation in humans.

The genetic and cellular malleability of the neurofibroma mouse models discussed here reveal important details about microenvironment participation in tumor formation that have general relevance for human cancer outside the context of Von Recklinghausen's Neurofibromatosis.

EXPERIMENTAL

Material and Methods

Animals and Reagents.

The Krox20; Nf1$^{flox/flox}$ mice utilized in these studies have been previously described (Zhu, et al., 2002), "Neurofibroma in NF1: Schwann cell origin and role of tumor environment," Science 296, 920-922. To generate Krox20; Nf1$^{flox/-}$ mice, we intercrossed Krox20; Nf1$^{flox/flox}$ mice with Nf1$^{+/-}$ mice. All procedures involving the use of animals were approved by the Institutional Animal Care and Use Committee at Indiana University School of Medicine. Chemicals were purchased from Sigma (St. Louis, Mo.) unless otherwise stated.

Adoptive Transfer of Hematopoietic Cells.

In order to evaluate the role of microenvironmental regulation of plexiform neurofibroma progression, bone marrow transplants were performed. Briefly, two million, syngeneic WT or Nf1$^{+/-}$ bone marrow cells from WT GFP or Nf1$^{-/-}$ GFP mice per recipient were adoptively transferred into young adult Krox20; Nf1$^{flox/flox}$ mice and Krox20; Nf1$^{flox/-}$ mice after treating them with 1100 rads of ionizing radiation administered over two split doses.

PET Imaging Analysis.

In order to verify and anatomically locate plexiform neurofibromas, combined [$^{18}$F] fluorodeoxyglucose ([$^{18}$F] FDG) PET and x-ray CT imaging were performed. When collecting CT images a template was placed over regions lateral to obtain on a standardized volume of interest (VOI) thereby enabling the researcher to quantify FDG uptake. Registered and overlaid CT image data was used to identify specific vertebrae (e.g., landmarks from L1 to S1). The operator then chose points along the spinal cord to determine the path of the spinal cord through between L1 and S1. Next, three circular regions-of-interest (ROI) are placed at interpolated points along the spinal cord to capture the spinal cord and the dorsal root ganglion regions. Finally, the circular ROI's are combined to create VOI's for the spinal cord, left dorsal root ganglion, and right dorsal root ganglion. FDG images are acquired at 45 minutes post injection of about 0.5-1.0 mCi of FDG via tail vein injection. All animals are given injections of FDG while awake and isoflurane anesthesia about 40 minutes post injection in order to immobilize the animals for imaging.

Figure 8:
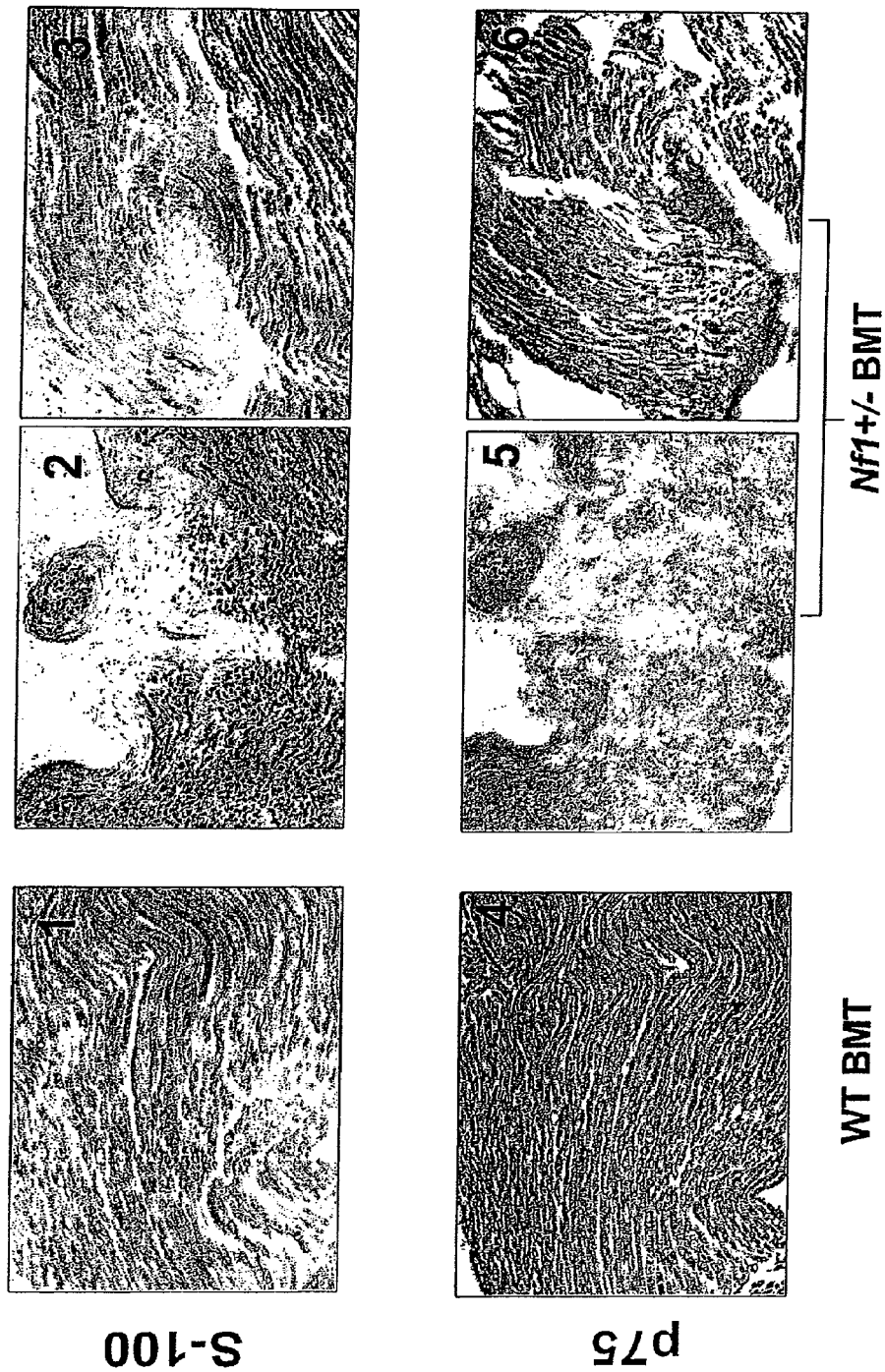
FIG. 8. Photomicrographs of tissue sample taken from mice. These images illustrate the identification of plexiform neurofibromas using FDG-PET. FDG-PET images and dissection of spinal nerves of a Krox20; Nf1$^{flox/flox}$ mouse and Krox20; Nf1$^{flox/-}$ mouse imaged at 9 months of age.
Figure 9:
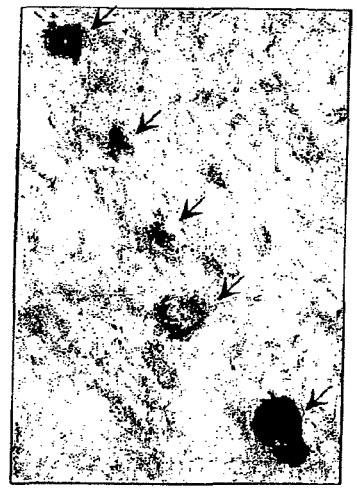
FIG. 9. Photomicrographs of a tissue samples stained with Toludine Blue and shown at 100× and 600× magnification, the arrows point to mast cells.
Figure 9:
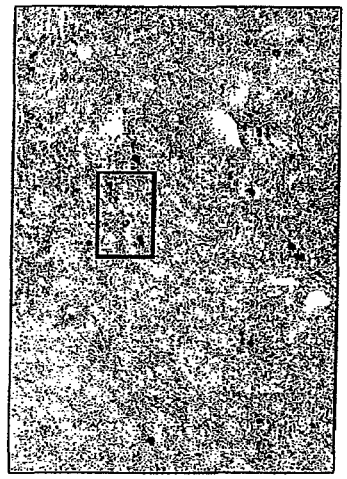
Figure 10:
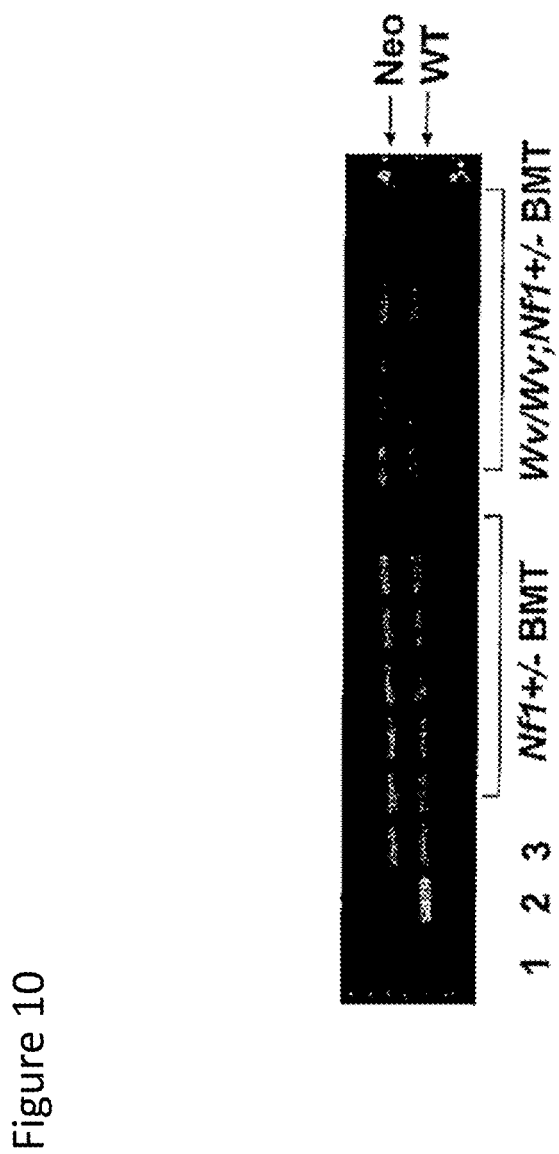
FIG. 10. Gel showing genotypic identification of DNA of individual myeloid progenitors isolated from bone marrow of irradiated Krox20; Nf1$^{flox/flox}$ recipients transplanted with Nf1$^{+/-}$; Wv/Wv bone marrow.
Figure 11A:
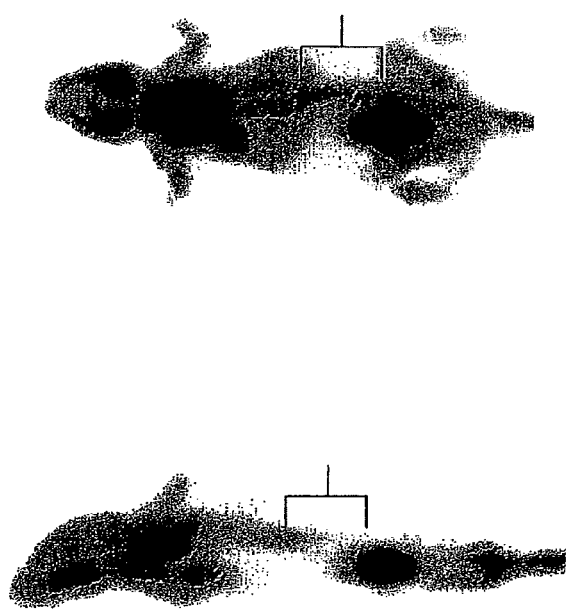
FIG. 11A Identification of plexiform neurofibromas using FDG-PET. FDG-PET images and dissection of spinal nerves of a Krox20; Nf1$^{flox/flox}$ mouse and Krox20; Nf1$^{flox/-}$ mouse imaged at 9 months of age.
Figure 11B:
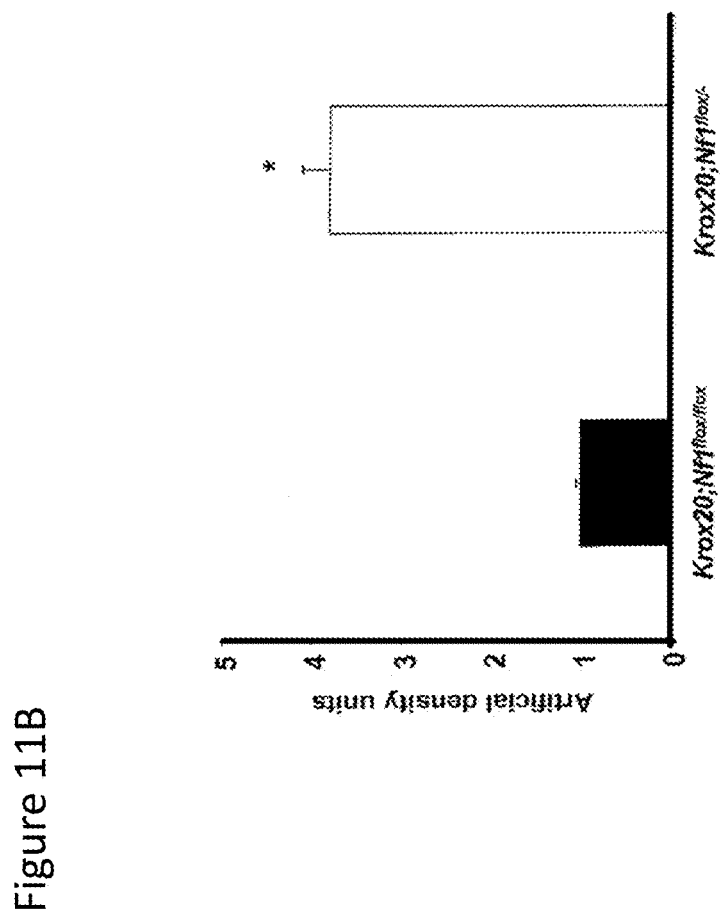
FIG. 11B. Graph showing the mean intensity of FDG-PET from the sciatic nerve region of interests in Krox20; Nf1$^{flox/-}$ and Krox20; Nf1$^{flox/flox}$ mice.
Figure 11C:
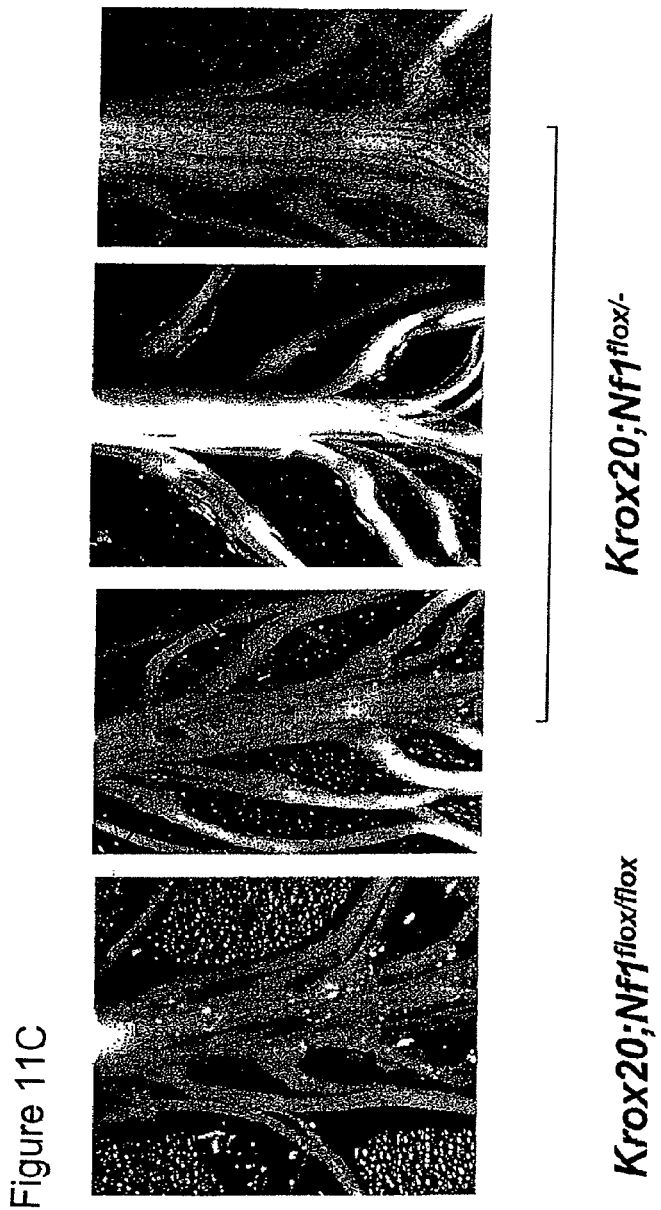
FIG. 11C. Photographs of the representative dissections from the dorsal root ganglia from a Krox20; Nf1$^{flox/flox}$ mouse (Panel 1) and Krox20; Nf1$^{flox/-}$ mice with PET positive tumors (Panels 2-4).
Figure 12:
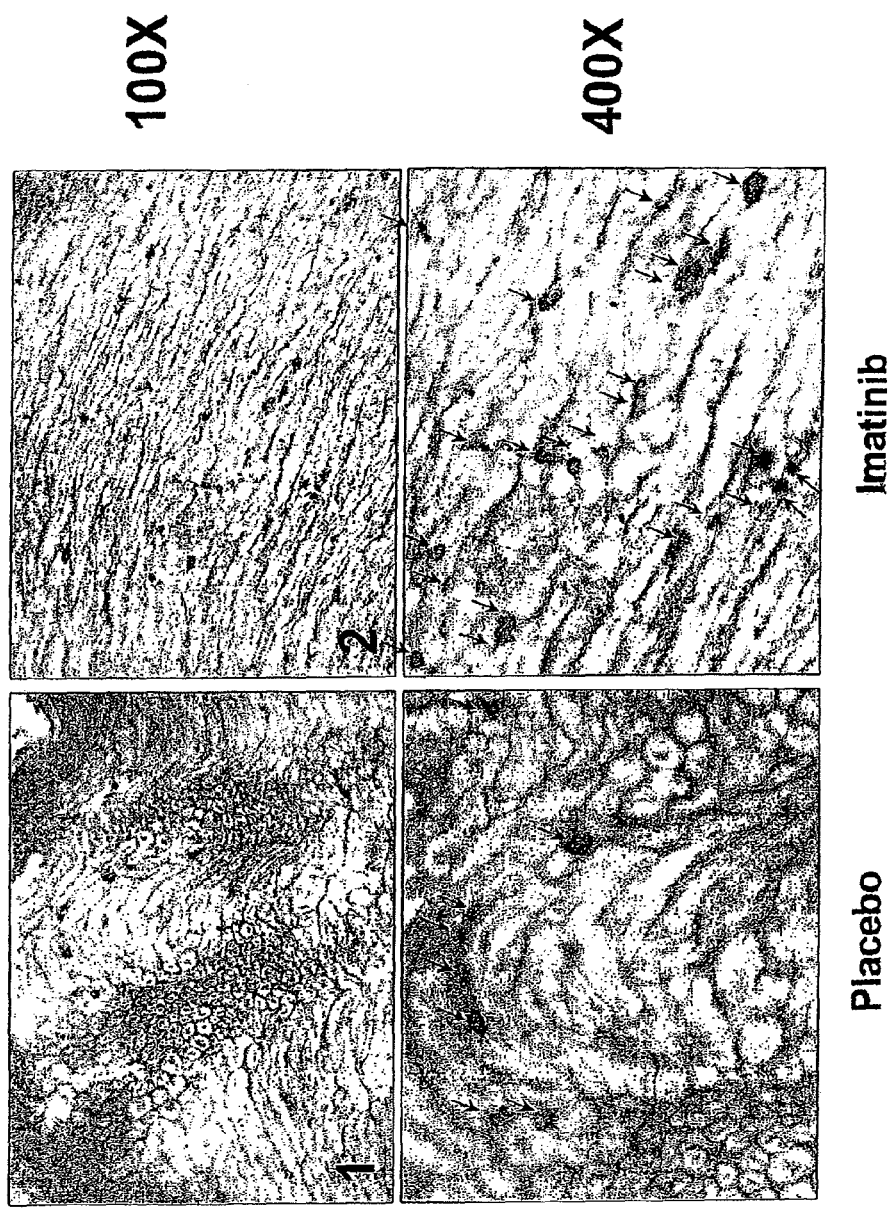
FIG. 12 Evaluation of apoptosis in plexiform neurofibromas using TUNEL following treatment with imatinib mesylate or placebo. Representative sections from plexiform neurofibromas treated with a placebo control (left Panel) or imatinib mesylate (right Panel). Arrowheads indicate TUNEL positive cells.

Preliminary imaging studies are conducted in non-tumorigenic Krox 20; Nf1$^{flox/flox}$ mice and in Krox20; Nf1$^{flox/-}$ mice that develop neurofibromas with full penetrance. In preliminary studies both experimental PET imaging and anatomic dissection of the dorsal root ganglia and proximal peripheral nerves failed to detect tumors in any mice prior to 6 months of age regardless of the genotype (data not shown). Similarly, there was little FDG uptake in Krox20; Nf1$^{flox/flox}$ mice in the lumbosacral region at 9 months of age (FIG. 8A). In contrast, an FDG PET scan of 9 month old Krox20; Nf1$^{flox/-}$ mice in which tumors are prevalent in the sciatic nerve, demonstrates a specific increased FDG-PET intensity in the lumbar region of the spine (FIG. 8A; arrows). Subsequent necropsy of the imaged animals provided correspondent verification of the FDG PET imaging identified tumors (FIG. 8B). Summary FDG-PET image data from a cohort of Krox20; Nf1$^{flox/-}$ mice versus a comparable age Krox20; Nf1$^{flox/flox}$ cohort is shown in FIG. 8C. These studies validate noninvasive FDG-PET imaging for identifying plexiform neurofibromas in Krox20; Nf1$^{flox/-}$ mice.

Dissection of Dorsal Root Ganglia.

Immediately after sacrificing them postmortem mice are perfused and fixed in 4% paraformaldehyde. The dorsal root ganglia and peripheral nerves are then dissected out under a dissection microscope. Mice whose tissue will be analyzed by electron microscopy analysis are perfusion fixed with 2% paraformaldehyde, 2.5% glutaraldehyde, and 0.1M cacodylate (pH7.4).

Measurement of Tumor Size.

In order to evaluate a tumor's size, an anatomic measurement of the dorsal root ganglia size is performed following measuring the largest possible width and length of the proximal dorsal root ganglia using a caliper. The volume of tumors is determined by establishing the approximate volume for a spheroid (e.g. 0.52× (width) 2× length).

Phenotypic Evaluation of the Donor Cells in Dorsal Root Ganglia.

To examine the cell type(s) from donor that reconstituted into the tumors, flow cytometric analysis was performed. Briefly, dorsal root ganglia was dissected out, minced, and digested by collagenase V. The single cell suspension was then admixed with anti CD117, CD31, or Col1A and FcεRI and antibodies. Populations were then separated using a fluorescence-activated cell sorter (Becton Dickson).

Histological Analysis.

To examine the morphology of the tumors in detail, paraffin sections were stained with hematoxylin and eosin (H&E). Given collagen accounts for approximately 60% of the dry weight of human plexiform neurofibromas, the tissue sections were also stained with Masson trichrome. To determine the existing of mast cells in the tumors, Alcian blue staining was performed.

Transmission Electron Microscopy.

Following perfusion fixation, tissues were dehydrated in a graded series of ethanol and acetone and embedded in Epon-Araldite (Electron Microscopy Sciences, Hatfield, Pa.).

Ultrathin sections (silver to gold) were stained with uranyl acetate and lead citrate and examined with a FEI Tecnai G2 electron microscope (Philips, Eindhoven, Netherlands).

Experiment 1

Figure 1B:
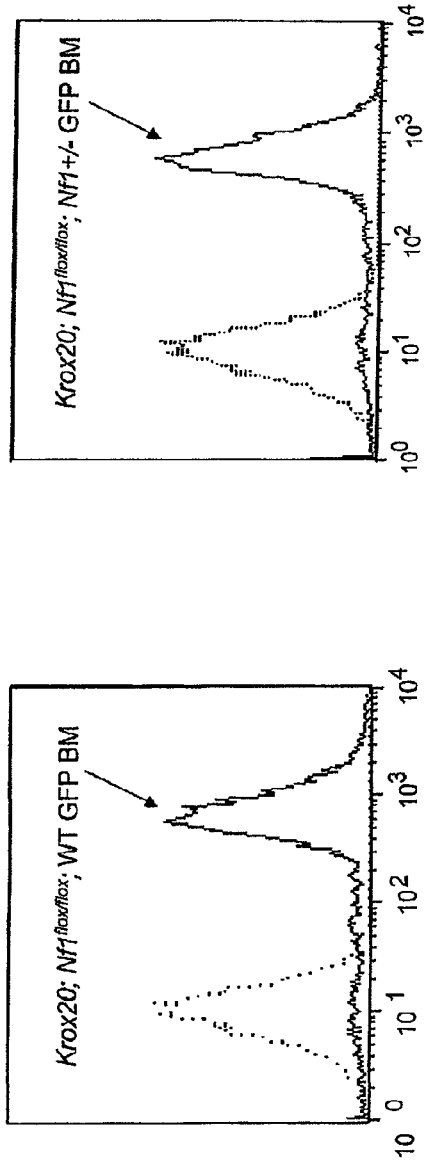
FIG. 1B. Traces generated using fluorescence cytometry. $Nf1^{+/-}$ bone marrow is necessary for plexiform neurofibroma formation in Krox20, $Nf1^{flox/flox}$ and Krox20; $Nf1^{flox/-}$ mice.

Adoptive Transfer of Nf1 Heterozygous Bone Marrow (BM) Reduces Tumor Associated Recipient Survival Referring now to FIG. 1, the schematic illustrates the genotypes of recipient mice, the genotypes of adoptively transferred cells following ionizing radiation of the recipients, and measurements obtained following transplantation. In order to test the hypothesis that heterozygosity of Nf1 in hematopoietic cells within the tumor microenvironment is responsible for the genetic haploinsufficiency required for neurofibroma formation, we transferred Nf1 heterozygous bone marrow into mice harboring two Krox20-Cre transgene ablated Nf1 alleles in approximately 10% of Schwann cells (Krox20; Nf1$^{flox/flox}$). Krox20; Nf1$^{flox/flox}$ mice are functionally wild type in all cell lineages and no neurofibromas are observed. As a complementary experiment, WT bone marrow cells were transplanted into mice containing a germline nullizygous allele of Nf1 and a foxed allele susceptible to recombination in the Schwann cell lineage as above (Krox20; Nf1$^{flox/-}$). Krox20; Nf1$^{flox/-}$ mice uniformly develop plexiform neurofibromas as previously described (Zhu et al., 2002). A portion of the Nf1$^{+/-}$ or WT bone marrow was adoptively transferred into recipients following ionizing radiation, and the development of plexiform neurofibromas and mortality associated with these tumors was monitored until 1 year of age.

Figure 2A:
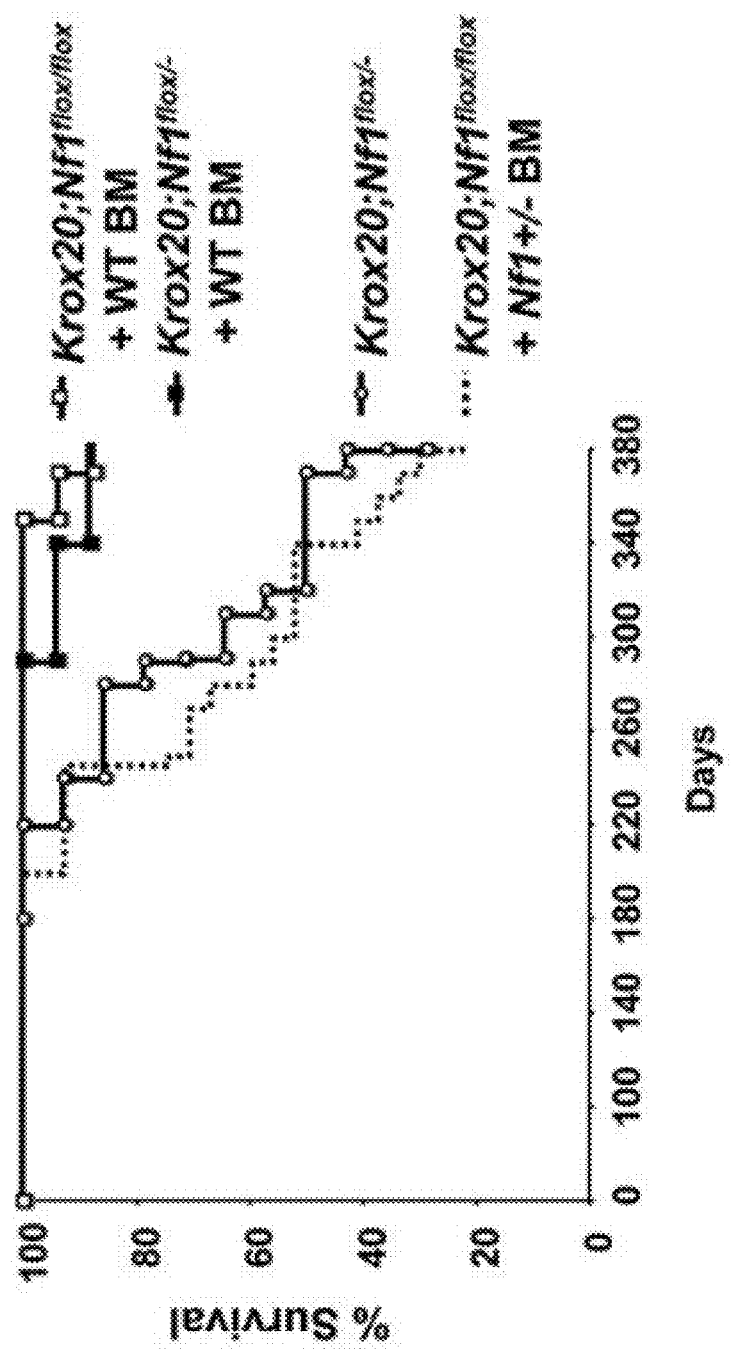
FIG. 2A. A Kaplan-Meier plot of percent survival (y-axis) as a function of time (x-axis) is shown. Krox20; $Nf1^{flox/flox}$ and Krox20; $Nf1^{flox/-}$ mice that were transplanted with $Nf1^{+/-}$ or WT bone marrow were followed until 1 year of age.

Referring now to FIG. 2A, the genotypes are indicated next to each plot. Mice were sacrificed once they exhibited clear signs of major morbidity. The Y-axis shows the percentage of the surviving mice. Comparisons of Krox20; Nf1$^{flox/flox}$+ Nf1$^{+/-}$ BM (dashed line) vs. Krox20; Nf1$^{flox/flox}$+ WT BM (open squares) (P<0.002); Krox20; Nf1$^{flox/flox}$+ Nf1$^{+/-}$ BM (dashed line) vs. Krox20; Nf1$^{flox/-}$ (open circles)—no significant difference. Krox20; Nf1$^{flox/-}$ (open circles) vs. Krox20; Nf1$^{flox/-}$+WT bone marrow (closed squares) (p<0.0.002). Six months after transplantation, the functional germline WT (Krox20; Nf1$^{flox/flox}$) recipients engrafted with heterozygous Nf1$^{+/-}$ bone marrow began to exhibit motor paralysis, weight loss and only 15% of mice survived the entire experimental period, see, e.g., FIGS. 2A & B. This mortality rate largely mirrored that previously observed in the germline heterozygous Krox20; Nf1$^{flox/-}$ mice (FIG. 2A). In contrast, approximately 90% of Krox20; Nf1$^{flox/flox}$ mice reconstituted with WT bone marrow were alive and exhibited no clinical features of plexiform neurofibroma formation (FIG. 2A). These data were corroborated by the converse experiment in which transplantation of WT bone marrow cells into germline heterozygous, Krox20; Nf1$^{flox/-}$, mice restored the survival to levels comparable to that of non-tumorigenic Krox20; Nf1$^{flox/flox}$ mice that contain intact bone marrow (FIG. 2A).

Figure 2B:
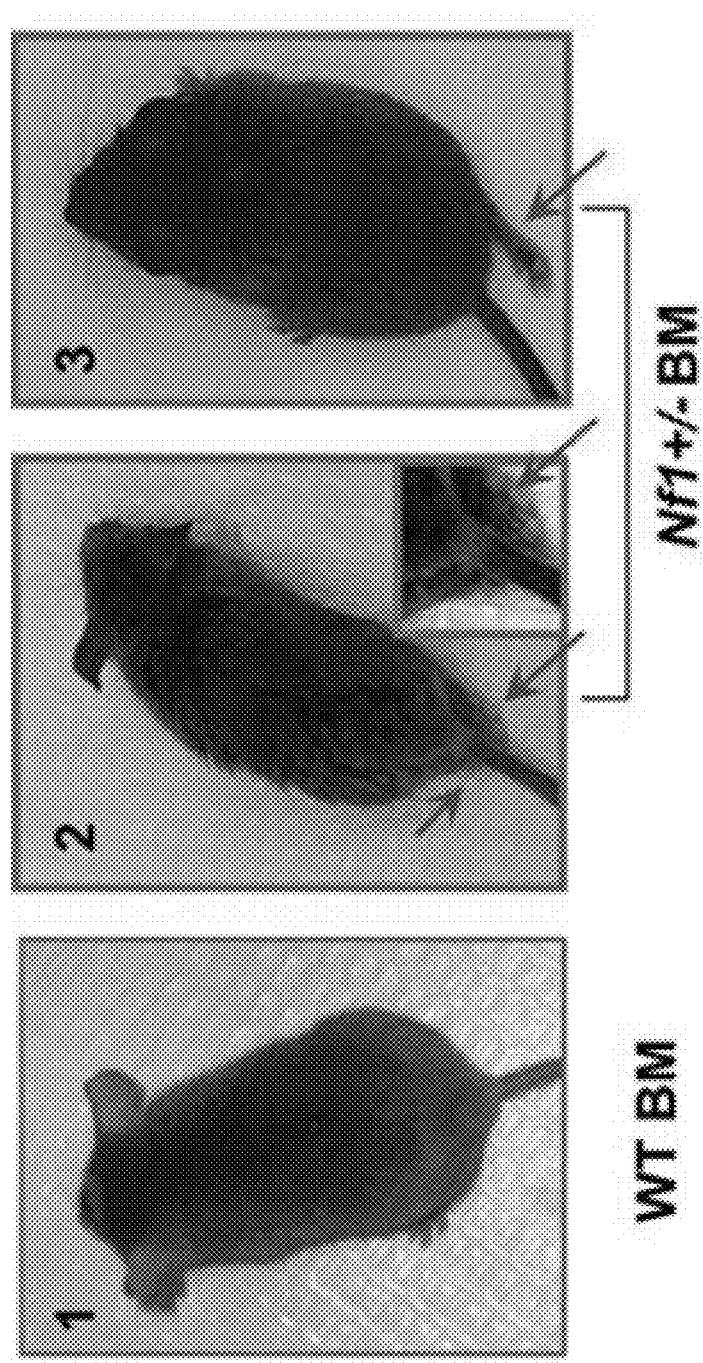
FIG. 2B. Photographs of Krox20; $Nf1^{flox/flox}$ mice transplanted with WT BM (1) or $Nf1^{+/-}$ BM (2-3).
Figure 2C:
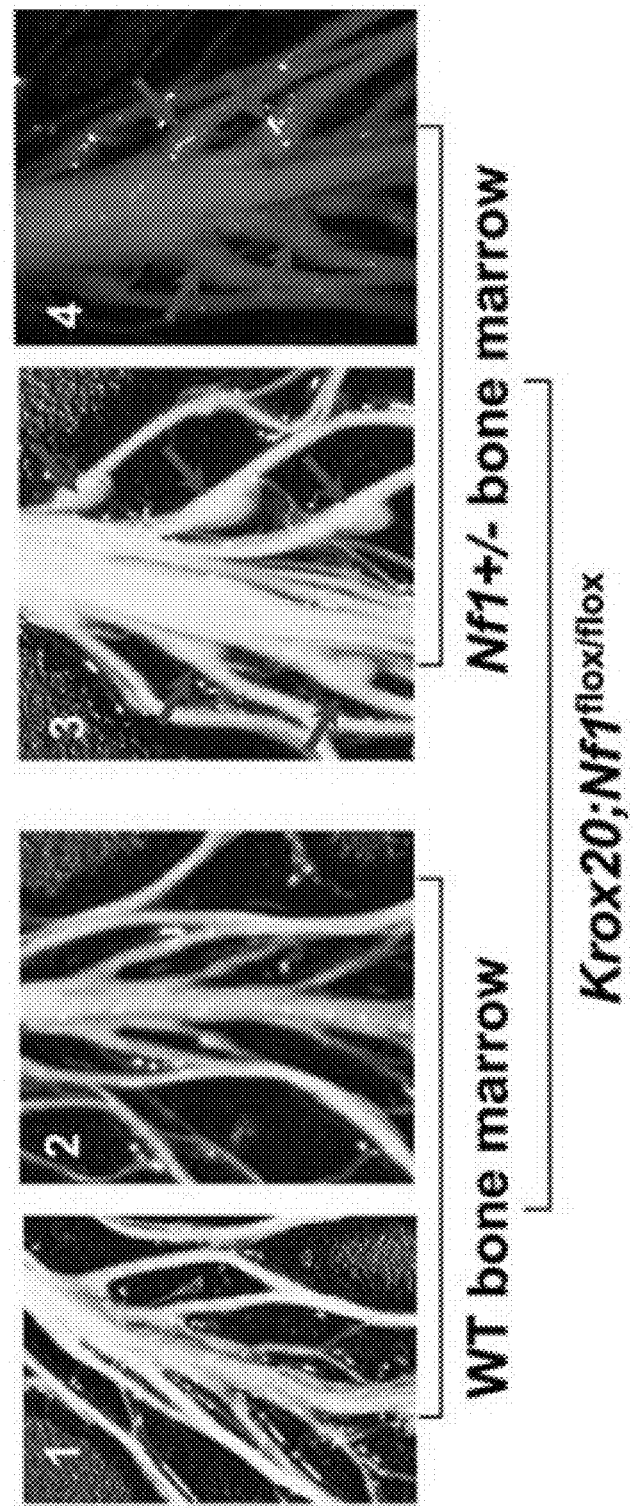
FIG. 2C. Photographs of dissections of dorsal root ganglia and peripheral nerves of Krox20; $Nf1^{flox/flox}$ mice that were transplanted with WT or $Nf1^{+/-}$ bone marrow. Arrowheads identify tumors in dorsal root ganglia and in peripheral nerves.

Referring now to FIG. 2C photographs of dissections of dorsal root ganglia and peripheral nerves of Krox20; Nf1$^{flox/flox}$ mice transplanted with either WT or Nf1$^{+/-}$ bone marrow. Arrowheads identify tumors in dorsal root ganglia and proximal peripheral nerves. Necropsy of the brains and spinal cords of the morbid mice revealed that 21 of 22 Nf1$^{+/-}$ bone marrow transplant recipients had an increased thickness of the entire spinal cord as compared to the spinal cords of non-symptomatic mice transplanted with WT bone marrow. This abnormal morphology resembles that of the tumorigenic Krox20; Nf1$^{flox/-}$ mice.

Referring now to FIG. 2C, photomicrographs of the dorsal root ganglia of mice with different genetic compositions the arrowheads identify ganglia serving limbs that exhibit motor paralysis. Panels 2 and 3 of FIG. 2C show the existence of discrete tumors arising from the dorsal root ganglia of Krox20; Nf1$^{flox/flox}$ mice transplanted with Nf1$^{+/-}$ bone marrow and these tumors were particularly prevalent in the sciatic nerves. Volumetric analysis of the tumors revealed a 3-6 fold increase in volume compared to unaffected dorsal root ganglia in mice that did not develop tumors. The large size and anatomic location of the tumors infiltrating the sciatic nerve and lumbosacral plexus, likely account for the observed behavioral abnormalities hind limb paralysis, hydronephrosis and enlarged, atonic bladder (FIG. 2B). In sum, these data indicate that the presence of NF1 heterozygous bone marrow in the context of Schwann cell loss of heterozygosity is sufficient to recapitulate the morbidity and peripheral nerve hyperplasia originally observed in Krox20; Nf1$^{flox/-}$ tumorigenic mice.

Experiment 2

Nf1$^{+/-}$ Bone Marrow (BM) Recipients Develop Plexiform Neurofibromas

Figure 3:
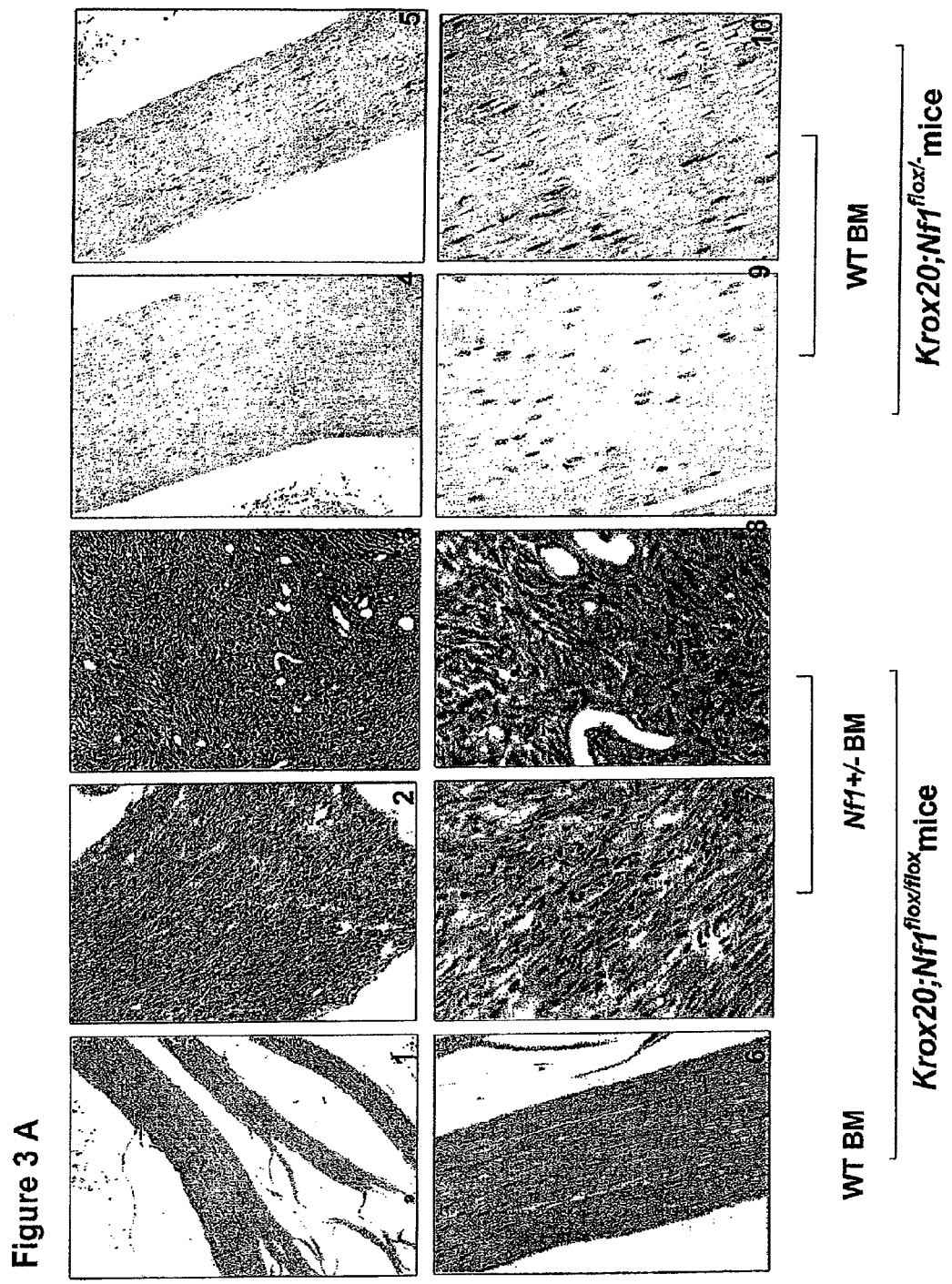
FIG. 3A. Hematoxylin and eosin (H&E) sections of dorsal root ganglia and proximal peripheral nerves.
FIG. 3B. Photographs of 200× magnification of sections stained with Masson's trichrome. The genotypes of donor bone marrow and recipient mice are indicated.
FIG. 3C. 200× magnification of sections stained with Alcian blue. Small arrowheads in Panels 2 and 3 identify mast cells. The large arrowheads in Panel 3 identify blood vessels.
FIG. 3D. Bar graph showing the difference in the number of mast cells between different genotypes. The lineages are isolated by FACS from tumors of Krox20; $Nf1^{flox/flox}$ mice transplanted with $Nf1^{-/-}$ BM.
FIG. 3E. Graphic presentation of phenotypic evaluation data of various bone marrow derived lineages using fluorescence cytometry. Bone marrow (panel 1) and tumor cells (panel 2) were isolated and sorted for EGFP+CD45.2 positive populations. Tumor associated CD45.2 cells were further separated to identify mast cell (panel 3), macrophage (panel 4), B-lymphocyte (panel 4) and T-lymphocyte populations. The proportion of each hematopoietic cell population within the tumor is indicated.
FIG. 3F. Gel showing genotyping of lineages isolated by FACS from tumors of Krox20; $Nf1^{flox/flox}$ mice transplanted with $Nf1^{+/-}$ BM. Arrowheads identify the amplified DNA products of the indicated alleles from the respective phenotypic lineages.
Figure 3:
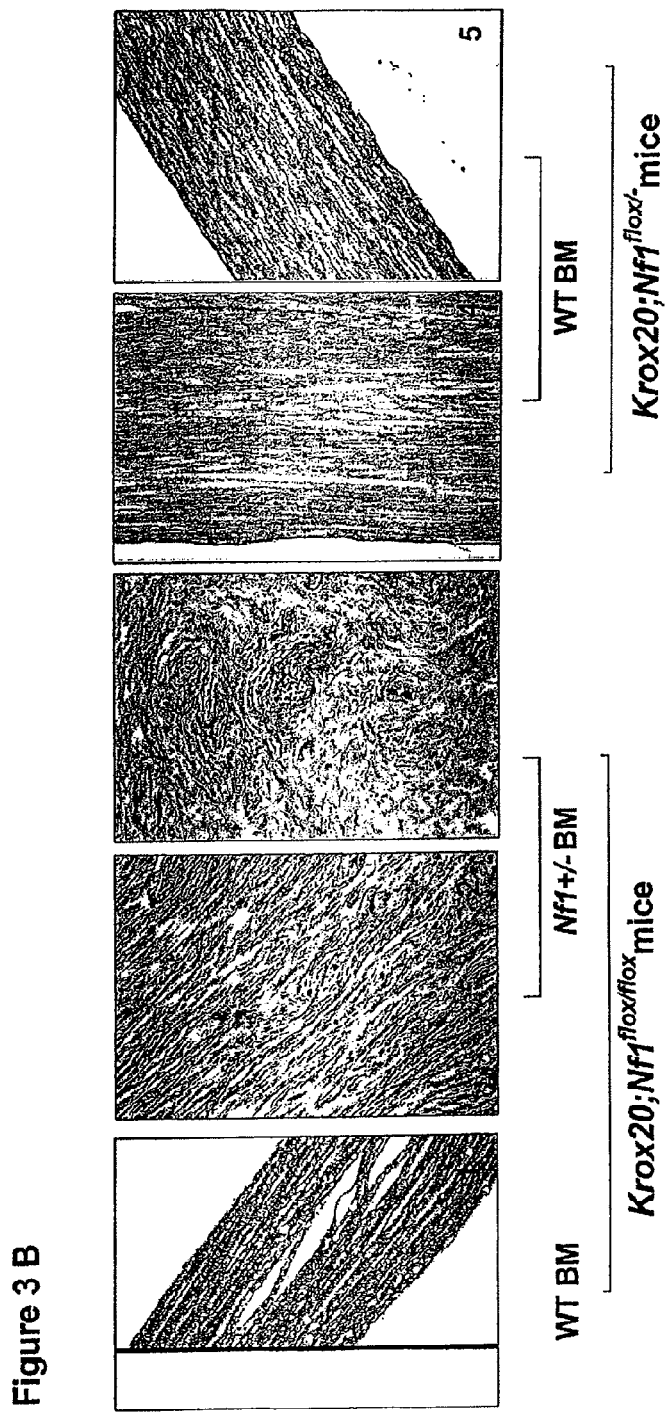
Figure 3:
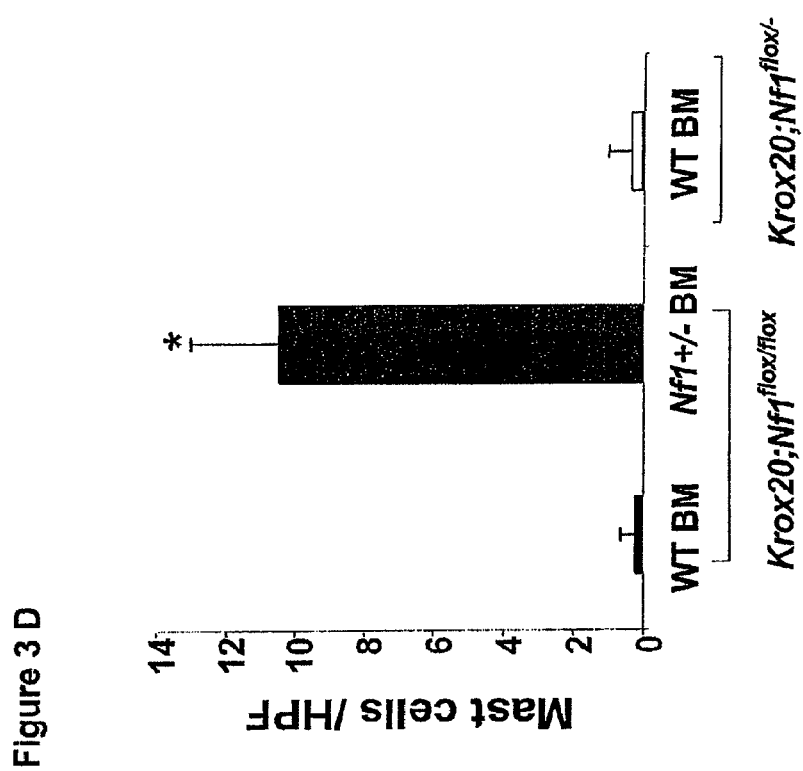
Figure 7:
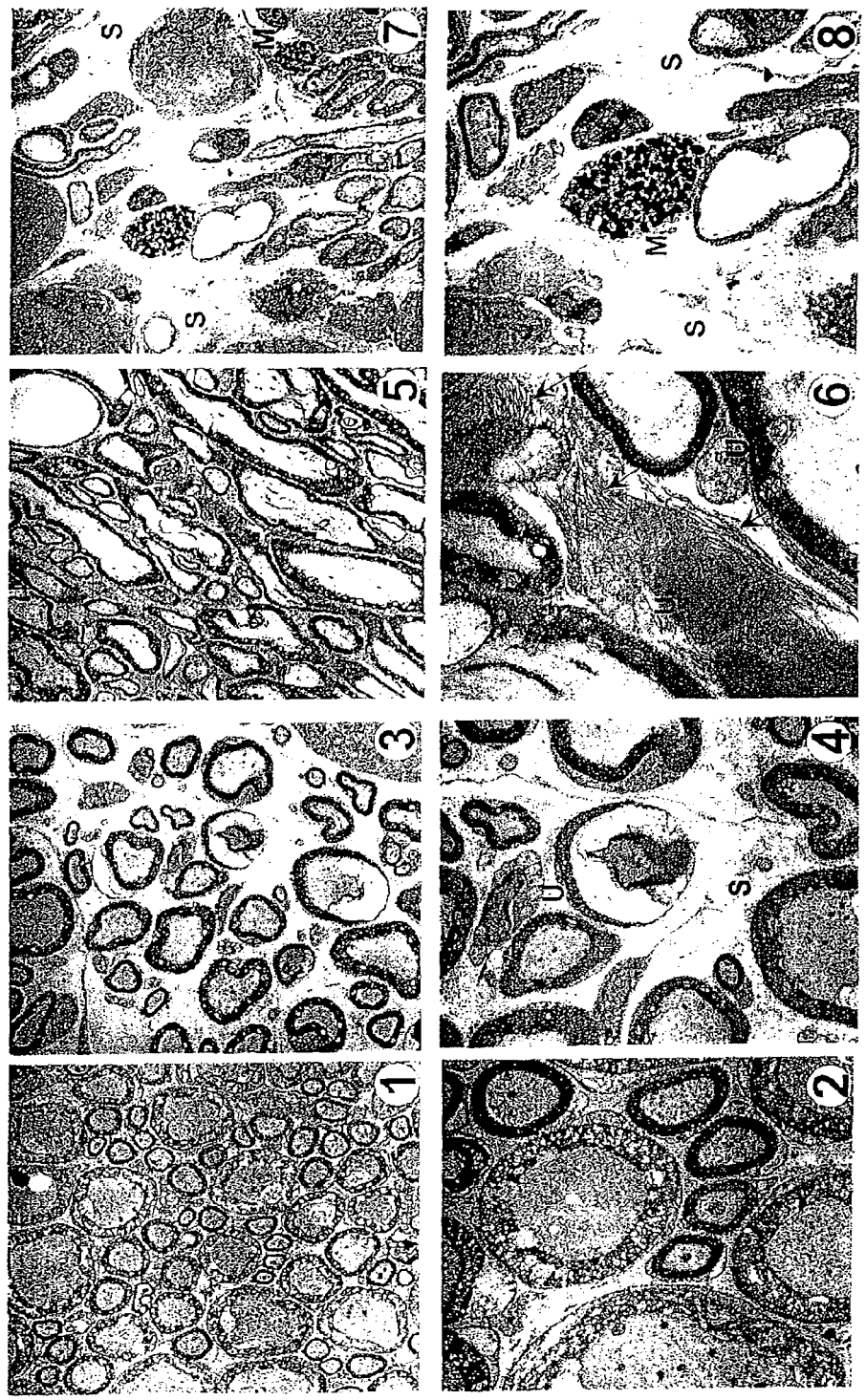
FIG. 7. Ultrastructural analysis of dorsal root ganglia by transmission electron microscopy. Panels 1-4, 750×, Panels 5-8, 1500×. Panel 1-2 proximal spinal nerves from a Krox20; $Nf1^{flox/flox}$ mouse transplanted with WT BM; Panels 3-8 proximal nerves from recipients transplanted with $Nf1^{+/-}$ BM. (U) unmyelinated axons; (S) indicates expansion of the endoneurial space. Arrowheads identify collagen bundles; (M) indicates mast cells infiltrating the tumor.

Referring now to FIG. 3A, pathologic analysis confirmed the presence of plexiform neurofibromas in Nf1 heterozygous bone marrow recipients Panels 1 and 6 are sections from a Krox20; Nf1$^{flox/flox}$ mouse transplanted with WT BM. Panels 2, 3, 7, 8 are from Krox20; Nf1$^{flox/flox}$ mice transplanted with Nf1$^{+/-}$ BM. Panels 4, 5, 9, 10 are from Krox20; Nf1$^{flox/-}$ mice transplanted with WT BM. The photos in upper Panels were taken with a light microscopy under 100×, whereas the photographs in the lower Panels were taken under 200×. The dorsal root ganglia from Krox20; Nf1$^{flox/flox}$ mice transplanted with Nf1$^{+/-}$ bone marrow exhibit classic histological features of human plexiform neurofibromas including disruption of normal architecture; wavy Schwann cells and infiltrating cells with hyperchromatic nuclei (FIG. 3A, Panels 7-8); excess collagen deposition (FIG. 3B, Panels 2, 3); angiogenesis (FIG. 3C, the large arrowheads in Panel 3 identify blood vessels); and classic ultrastructural abnormalities (FIG. 7). In FIG. 7, Panels 1-4, 750×, Panels 5-8, 1500×. Panels 1-2 proximal spinal nerves from a Krox20; Nf1$^{flox/flox}$ mouse transplanted with WT BM; Panels 3-8 proximal nerves from recipients transplanted with Nf1$^{+/-}$ BM. In these photographs (U) denotes unmyelinated axons; (S) indicates expansion of the endoneurial space; arrowheads identify collagen bundles; and (M) indicates mast cells infiltrating the tumor. In contrast, the nerves from either Krox20; Nf1$^{flox/flox}$ or Krox20; Nf1$^{flox/-}$ mice transplanted with WT marrow exhibited normal appearing, evenly distributed, nuclei throughout sections of the dorsal root ganglia and proximal peripheral nerves, (see, for example, FIG. 3A, Panels 1, 4-6, and 9-10) and no evidence of collagen deposition. Tumors isolated from Krox20; Nf1$^{flox/flox}$ mice transplanted with Nf1$^{+/-}$ bone marrow have histologic features of plexiform neurofibromas.

Referring now to FIG. 3B, Panels 1, 4-5, neovascularization, and retained normal ultra-structural morphology (FIG. 7). Neurofibromas are complex tumors comprising multiple cell types in which LOH is uniquely present in Schwann cell lineage (Zhu et al., 2002). Mast cell infiltration is characteristic of human and murine plexiform neurofibromas (Zhu et al., 2002). In the murine model for this condition used herein, we observe peripheral nerve infiltration by mast cells preceding tumor appearance. Accordingly, the heterozygous bone marrow of reconstituted Krox20; Nf1$^{flox/flox}$ mice also exhibited extensive mast cell infiltration (FIG. 3C, Panels 2-3). Fluorescence cytometry is used to purify the endothelial cells (CD31), fibroblasts (Col1A), and hematopoietic cells (c-Kit, CD 117) in the neurofibromas of Krox20; Nf1$^{flox/flox}$ mice transplanted with Nf1$^{+/-}$ bone marrow.

Referring now to FIG. 3D, arrowheads identify the amplified DNA products of the indicated alleles from the respective phenotypic lineages. Surprisingly, subsequent genotyping showed that only the c-Kit population, that also express FcεRI (not shown), harbored the Nf1 null allele (FIG. 3D). These data are consistent with the appearance of bona fide plexiform neurofibromas in the reconstituted Krox20; Nf1$^{flox/flox}$ including homing of the transplanted heterozygous mast cells to the sites of Nf1 nullizygous Schwann cells.

Referring now to FIG. 3E, bone marrow (BM) (band 1- and tumor cells (panel 2) are isolated and sorted by EGFP+; CD45, 2 positive populations. Tumor associated CD45.2 cells are further separated in order to mast cells (panel 3), macrophages (panel 4), B-lymphocytes (panel 4) and t-lymphocytes (panel 5). The graphs indicate the populations of each hematoporetic cell population within the tumor.

Figure 3F:
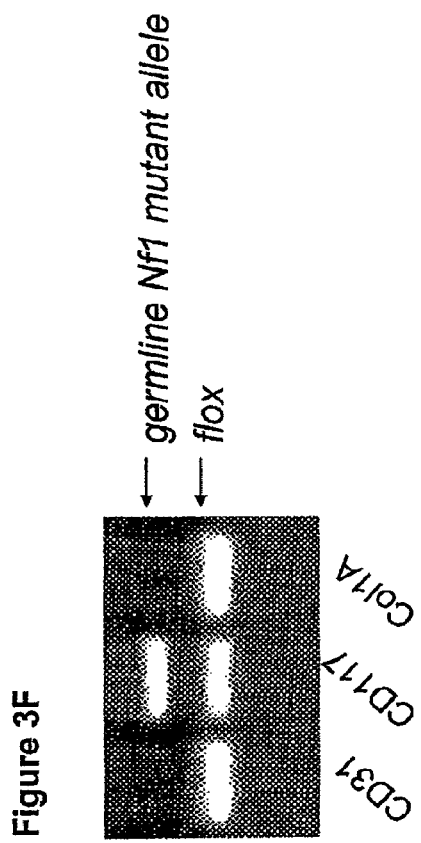

Referring now to FIG. 3F, the genotypes of lineages isolated by FACS from tumors of Krox20; Nf1$^{flox/flox}$ mice transfected with Nf1$^{+/-}$ Bone Marrow (BM). The arrows in FIG. 3F, point to bands on the gel formed by amplified DNA products of the identical alleles isolated from the indicated phenotypic lineages.

Nf1$^{+/-}$ Bone Marrow Mediated Tumor Formation Requires c-Kit.

The only Nf1 heterozygous cells detected in the reconstituted plexiform neurofibromas were derived from bone marrow. This finding is consistent with our previous in vitro and in vivo observations implicating a mast cell haploinsufficiency requirement in tumor formation. The c-kit receptor tyrosine kinase (RTK) is thought to control many aspects of mast cell development and function. We have reported that c-Kit activity appears to govern migration, proliferation, and survival of Nf1$^{+/-}$ bone marrow derived mast cells. We hypothesized a correlation between the conditions and tested the effort of genetic disruption of c-kit activity in Nf1$^{+/-}$ bone marrow cells transplanted into Krox20; Nf1$^{flox/flox}$ mice on tumor progression.

Genetic disruption of c-kit in adoptively transferred Nf1$^{+/-}$ bone marrow prevents the genesis of plexiform neurofibromas in recipient Krox20; Nf1$^{flox/flox}$ mice. Briefly, Nf1$^{+/-}$ mice were independently intercrossed with two hypomorphic strains of mice that have inhibited mast cell mobilization by virtue of point mutations in the c-kit receptor that reduce kinase activity 85% (W41/W41) to 95% (Wv/Wv), respectively.

Figure 4A:
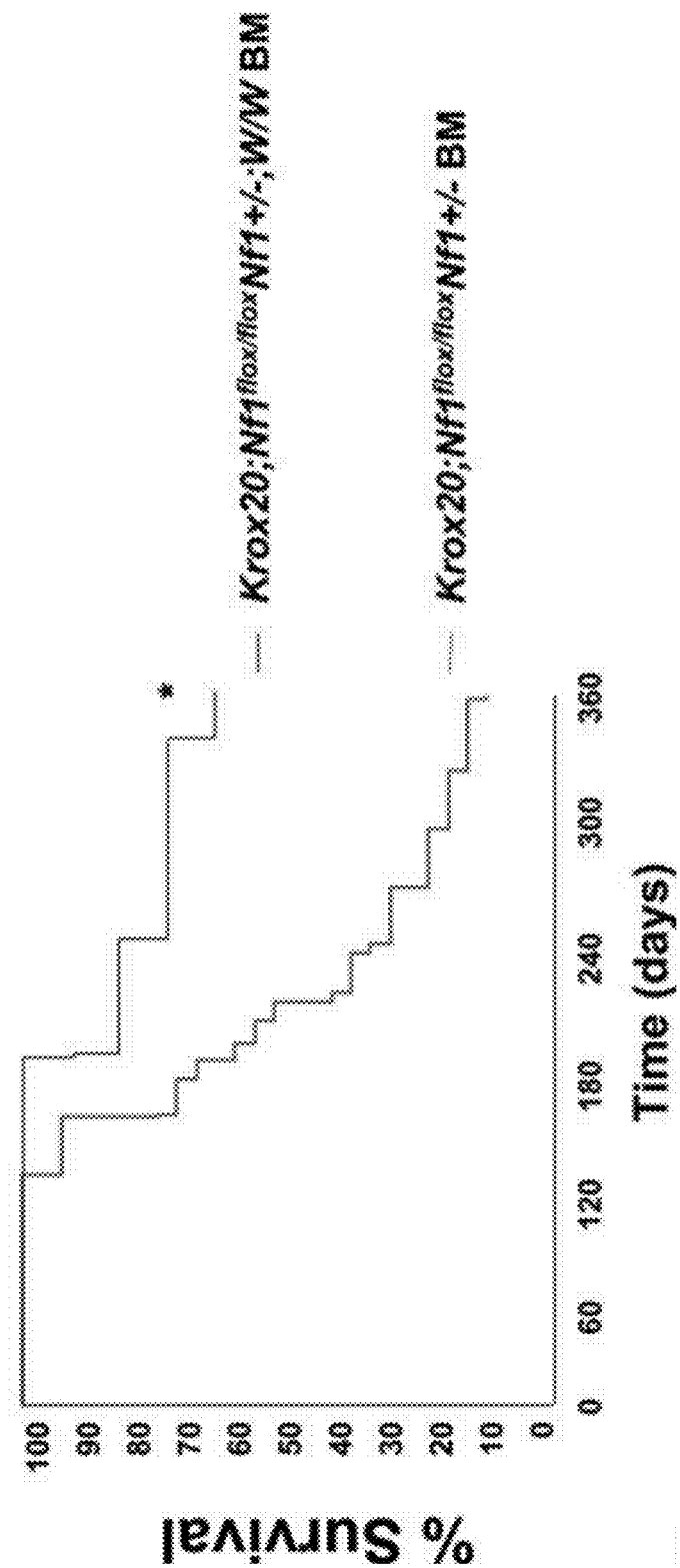
FIG. 4A. A Kaplan-Meier plot of percent survival (y-axis) as a function of time (x-axis) is shown.
Figure 4B:
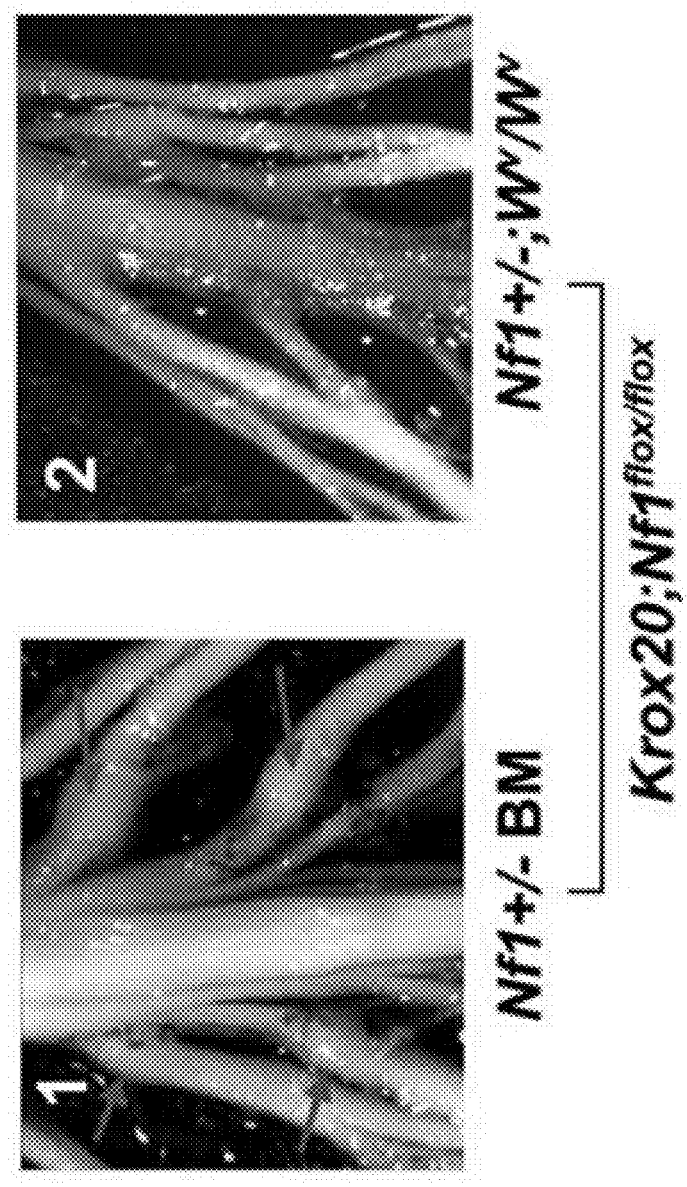
FIG. 4B. Photographs of the spinal cord and dorsal roots of Krox20; $Nf1^{flox/flox}$ mice transplanted with WT BM (panel 1) or $Nf1^{+/-}$ BM (panel 2). Arrowheads identify tumors in proximal nerves.

Referring now to FIG. 4A. The bone marrow from either Nf1$^{+/-}$; Wv/Wv or Nf1$^{+/-}$; W41/W41 doubly mutant mice was transplanted into five and ten Krox20; Nf1$^{flox/flox}$ mice respectively. Morbidity of mice engrafted with Nf1$^{+/-}$; W mutant marrow was significantly reduced as compared to Nf1$^{flox/flox}$ mice transplanted with Nf1$^{+/-}$ bone marrow Krox20; Nf1$^{flox/flox}$ mice were transplanted with Nf1$^{+/-}$ or Nf1$^{+/-}$; W mutant bone marrow were followed for 1 year. The genotypes and statistical significance between the two groups are indicated. Accordingly, in contrast to recipients of bone marrow, the dorsal root ganglia and proximal peripheral nerves from the Krox20; Nf1$^{flox/flox}$ mice transplanted with Nf1$^{+/-}$; W mutant marrow have normal morphology and do not exhibit hypertrophy or evidence of tumors (FIG. 4B). These results support the hypothesis that Nf1 haploinsufficiency originates in bone marrow and further refine the identity of the active component to a c-Kit dependent cell type.

Figure 4C:
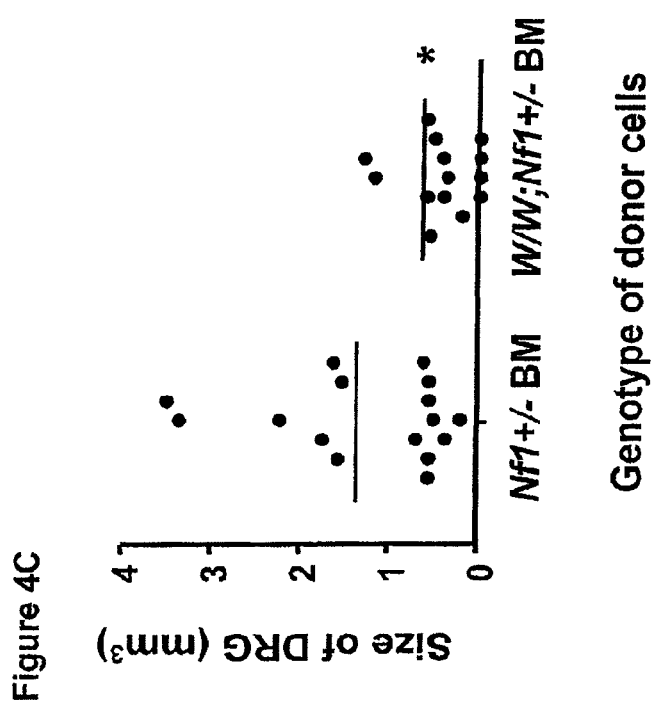
FIG. 4C. Graph illustrating Dorsal Root Ganglia (DRG) size measured with donor cells of differing genotype.
Figure 4:
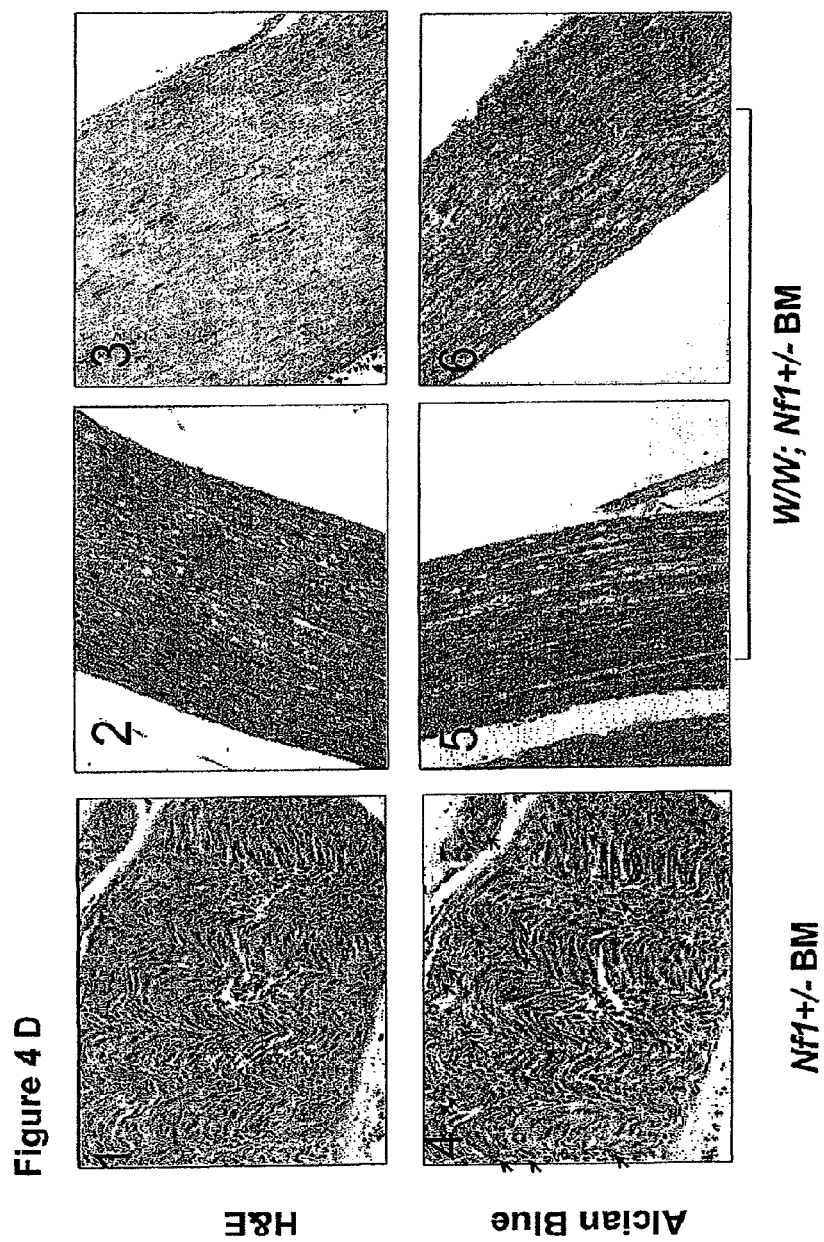
FIG. 4D. Photographs of representative histologic sections of dorsal root ganglia and proximal spinal nerves of Krox20; $Nf1^{flox/flox}$ mice transplanted with $Nf1^{+/-}$ or $Nf1^{+/-}$; W/W mutant marrow.

Referring now to FIG. 4C a graph of the volume of individual dorsal root ganglia (DRG) from the sciatic nerves of Krox20; Nf1$^{flox/flox}$ mice as a function of genotype are shown. Each individual dot represents the volume of an individual DRG and the lines represent the mean volume from the respective experimental groups. Recipients reconstituted with Nf1$^{+/-}$ bone marrow cells have significantly higher mean sciatic nerve DRG volumes than mice that were reconstituted with Nf1$^{+/-}$ bone marrow that also contains a mutation in the c-kit receptor that inactivates the c-kit pathway (Nf1$^{+/-}$; W/W).

Referring now to FIG. 4D, the sections shown in Panels 1-3 are H&E stained. The sections in Panels 4-6 are stained with Alcian blue. The arrow heads highlight mast cells. The genotypes of the adoptively transferred bone marrow are indicated below the respective columns of Panels.

Experiment 4

To assess the activity of imatinib mesylate and other potential pharmacologic agents on tumor burden we validated a noninvasive fluoridinated deoxyglucose positron emission tomography FDG-PET imaging protocol permitting identification and longitudinal observation of plexiform neurofibromas in Krox20; Nf1$^{flox/-}$ mice (see also the methods section and FIG. 8).

Figure 5B:
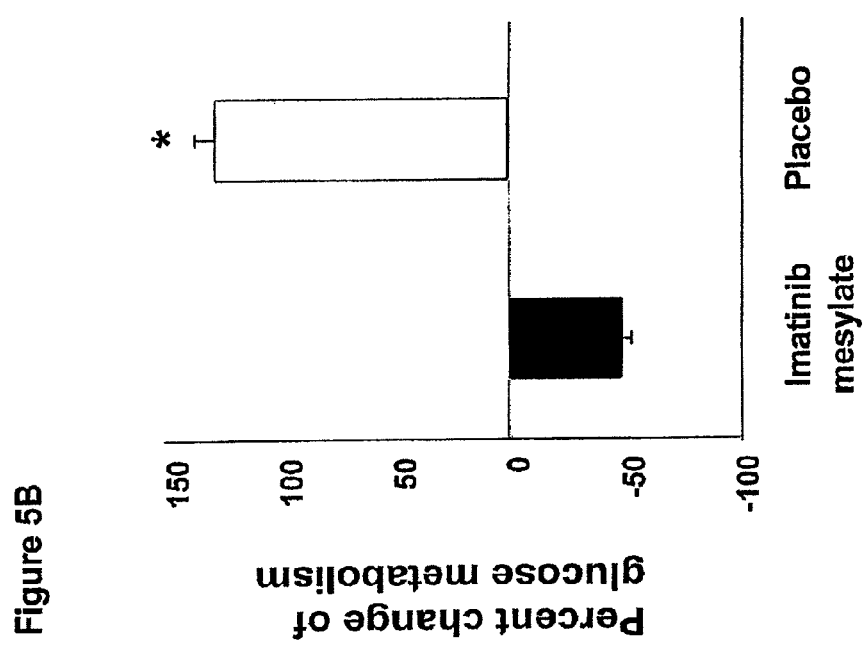
FIG. 5B. Graphic summary of changes in mean FDG-PET intensity after a 12 week treatment with imatinib mesylate or PBS.
Figure 5:
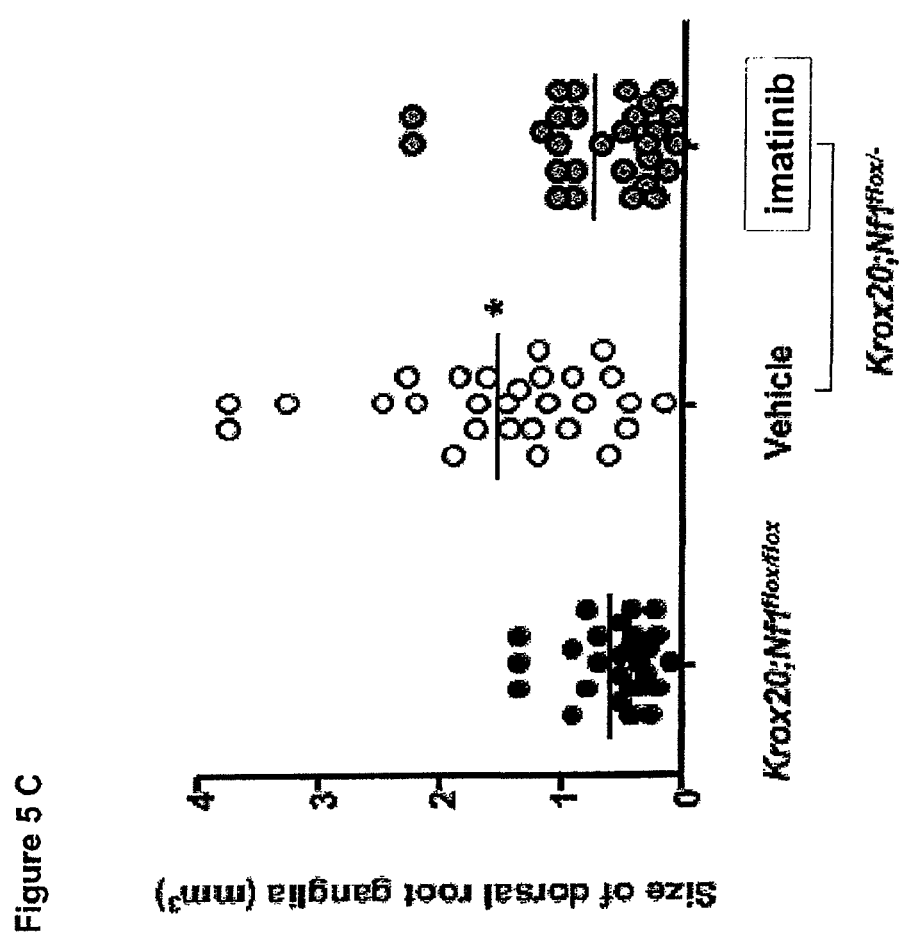
FIG. 5A. PET images illustrating effects of treating of Krox20; $Nf1^{flox/-}$ mice with imatinib mesylate.
FIG. 5C. Graphic representation of the data collected by dissecting certain peripheral nerves.
FIG. 5D. Photographs showing histological analysis of the Krox20; $Nf1^{flox/-}$ mice treated with imatinib mesylate or placebo.
FIG. 5E. Bar graph showing mast cell Number/HPF plotted as a function of treatment with and without Imatnib mesylate.
FIG. 5F. Bar graph showing the number of Tunnel Positive Cells/HPF plotted as a function of treatment with and without Imatnib mesylate.
Figure 5:
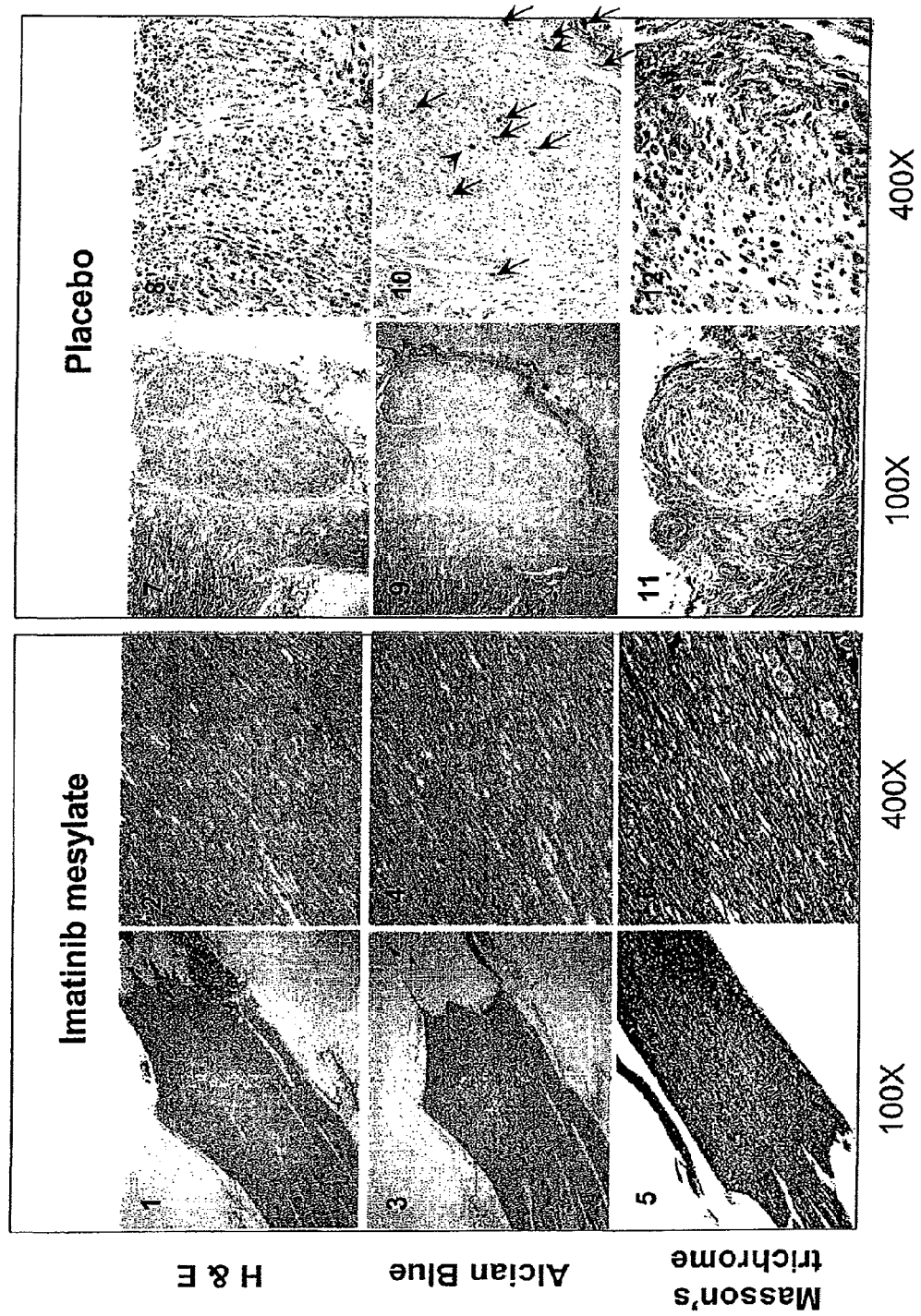

Referring now to FIG. 5A, images change in mean FDG-PET positive tumors after a 12 week treatment with imatinib mesylate. The regions of interest, the temporal sequence of scans in 3 individual mice, and the experimental treatment groups are identified. We next identified cohorts of 8 to 9 month old Krox20; Nf1$^{flox/-}$ mice with confirmed PET positive uptake in the region of the sciatic nerve for oral treatment with either 250 mg/kg/day of imatinib mesylate or a placebo control (PBS). FDG-PET imaging studies followed to evaluate the evolution of the tumors. Representative FDG-PET axial slices of affected nerves from three mice imaged before and after treatment with imatinib mesylate or PBS for three weeks are shown. As predicted, increased FDG uptake was seen in Krox20; Nf1$^{flox/-}$ animals lateral to the spine prior to treatment with either imatinib mesylate or PBS (FIG. 5A, Panels 1, 3, 5). Strikingly, FDG uptake was qualitatively reduced in the Krox 20; Nf1$^{flox/-}$ mice treated with imatinib mesylate (FIG. 5A, Panels 2-4) compared to the PBS controls (FIG. 5A, Panel 6). To carefully quantitate the FDG-PET intensity in all treated animals, a standardized region of interest (ROI) was utilized in each animal to extract quantitative FDG uptake values (mCi/ml tissue). Three dimensional ROIs in the shape of cylinders were utilized to encapsulate the areas lateral to the spinal column with the ROI cylinders and specific vertebrae landmarks from L1 to S1 were used in all cases to assure consistency. Representative results from one experimental animal, before and after treatment, are shown in Panels 7-8 (FIG. 5A). These images illustrate that treatment with imatinib mesylate reduces tumor size in this animal Referring now to FIG. 5B, a summary of PET imaging results presented in graphic form for the sciatic nerve region ROIs of one cohort of 12 experimental mice are plotted. Overall, the mice treated with imatinib mesylate had a mean 50% reduction in FDG-PET uptake after treatment (p<0.035). In contrast, the metabolic activity of the tumors in the cohort treated with PBS had a modest but not significant increase in the FDG uptake ratio comparable to the progressive uptake in FDG observed as a function of time in emerging plexiform neurofibromas in Krox20; Nf1$^{flox/-}$ mice.

To determine whether a change in metabolic activity (FDG uptake) directly correlated with histological changes in the tumors, the imaged cohorts were sacrificed, the spinal cords were examined, and sections were prepared for histologic evaluation.

Referring now to FIG. 5C, mean volume of dorsal root ganglia from all sciatic nerves of Krox20; Nf1$^{flox/-}$ mice treated with vehicle placebol vs. imatinib mesylate (n=28 in vehicle controls, and n—28 in the gleevec treated group). The solid line indicates the mean volume of each respective group. Each symbol indicates the volume of an individual nerve. At post mortem, we also compared the volumes of all dorsal root ganglia from an age equivalent cohort of Krox20; Nf1$^{flox/flox}$ mice. Consistent with the FDG-PET imaging studies, there was a clear decrease in dorsal root ganglia volume in the imatinib mesylate treated group as compared to the PBS treated group.

Histological evaluation of the dorsal root ganglia and proximal surrounding nerves in mice treated with either imatinib mesylate or PBS was also conducted. Referring now to FIG. 5D, representative sections are shown following H&E staining, Alcian blue staining, and Masson's trichrome staining. The experimental therapy, the stains utilized to prepare the specimens, is indicated on the left side of the figure. The magnification of the images in each set of Panels is shown across the bottom of the figure. As indicated by the column headings, samples shown in Panels 1-6 were obtained from mice treated with imatinib mesylate; samples shown in Panels 7-12 are obtained from mice treated with only a placebo. The arrowheads in Panel 10 identify mast cells found on the respective sections. Qualitatively, there is a distinct disruption of the normal nerve architecture and an increase in cellularity in nerves harvested from placebo treated mice compared to imatinib mesylate treated mice. This is illustrated in tissue sections showing the distal dorsal root and proximal nerve segments (FIG. 5D, Panels 1-6 compared to Panels 7-12). Further, there is a marked reduction in the number of mast cells in nerves dissected from mice treated with imatinib mesylate compared to PBS treated controls (FIG. 5D, Panels 3, 4 vs. Panels 9, 10). Collectively, the PET, gross anatomic and histological data identify the potential for imatinib mesylate to reduce tumor volume in Krox20; Nf1$^{flox/-}$ mice.

Figure 5E:
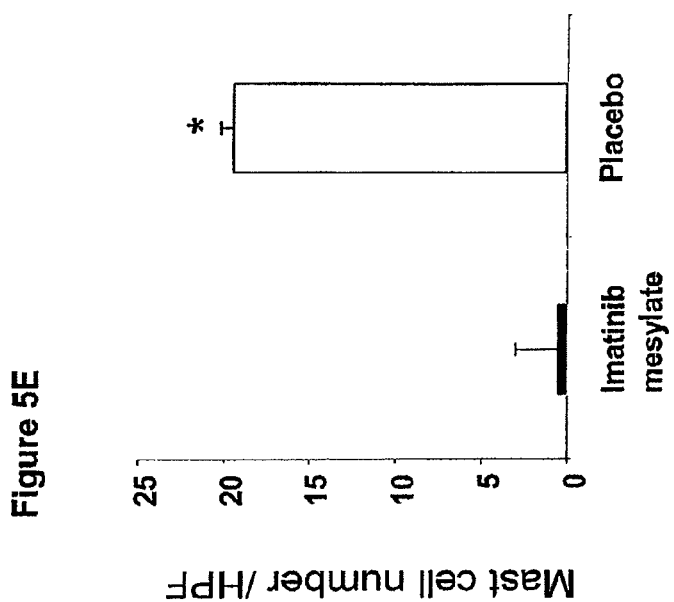
Figure 5F:
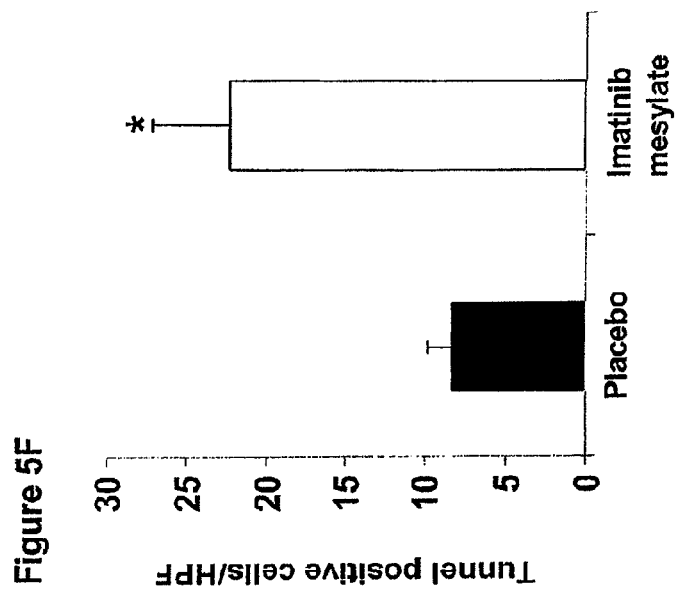

Referring now to FIG. 5E a bar graph illustrating a dramatic difference in the number of mast cells between mice treated with imatinib and mice that were not treated with the compound. Referring now to FIG. 5F, a bar graph illustrating a that there are fewer Tunnel Positive Cells/HPF in samples taken from mice treated with imatinib mesylate versus mice not treated with the compound.

One limitation of our mouse model is the animal's short lifespan. Therefore we cannot predict on the basis of our mouse studies how long-lived tumors might be expected to respond. It is conceivable that over time, tumor cells may accrue additional properties that render them independent of certain early paracrine events such as the mast Schwann cell interaction.

Experiment 5

Compassionate Use Treatment with Imatinib Mesylate of a Child Presenting with a Plexiform Neurofibroma Plexiform neurofibromas primarily present in infants and young children with NF1 are frequently characterized by rapid growth and invasion into adjacent organs often resulting in impairment of normal organ function. In addition, these tumors have a high likelihood of progressing to malignancy for which there is no cure. Even when benign, these tumors can be life threatening and present major clinical challenges as surgical treatment has limited effectiveness and there are no widely acceptable alternative therapies. A three year-old child presenting the classic clinical stigmata of NF1, including a large trigeminal plexiform neurofibroma, presented to the pediatric oncology clinic with life threatening airway compression. Based on our current studies in the murine model for this and related conditions, the attending physician placed the child on 350 mg/m2/dose of imatinib mesylate for a limited trial.

Figure 6:
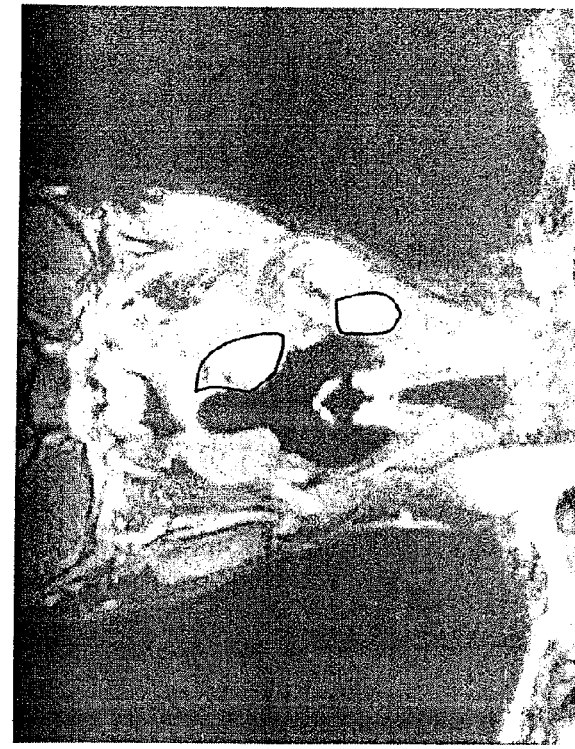
FIG. 6. MRI scans of a patient with plexiform neurofibromas before and after treatment with imatinib mesylate.
Figure 6:
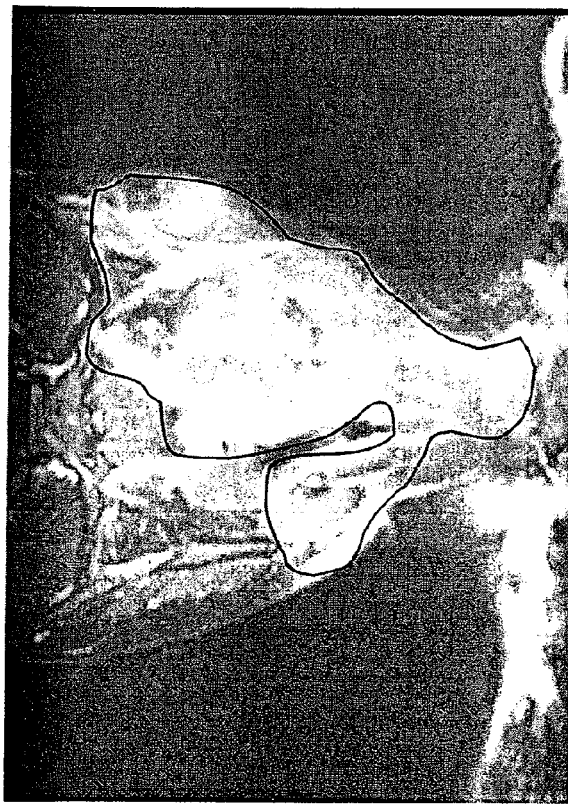

Referring now to FIG. 6, evaluation of imatinib mesylate efficacy in an index patient with a plexiform neurofibroma. The periphery of the tumor is traced in both Panels by a thick dark line. Sagital MRI scans of the head and oropharynx of an NF1 patient with a plexiform neurofibromas before (panel 1) and 3 months following treatment with imatinib mesylate (panel 2). MRI scans before and after three months of treatment revealed a remarkable approximately 70% reduction in tumor volume (FIG. 6). Following treatment for six months with no observed side effects, the patient went off treatment for six months without a recurrence of symptoms.

Figure 13A:
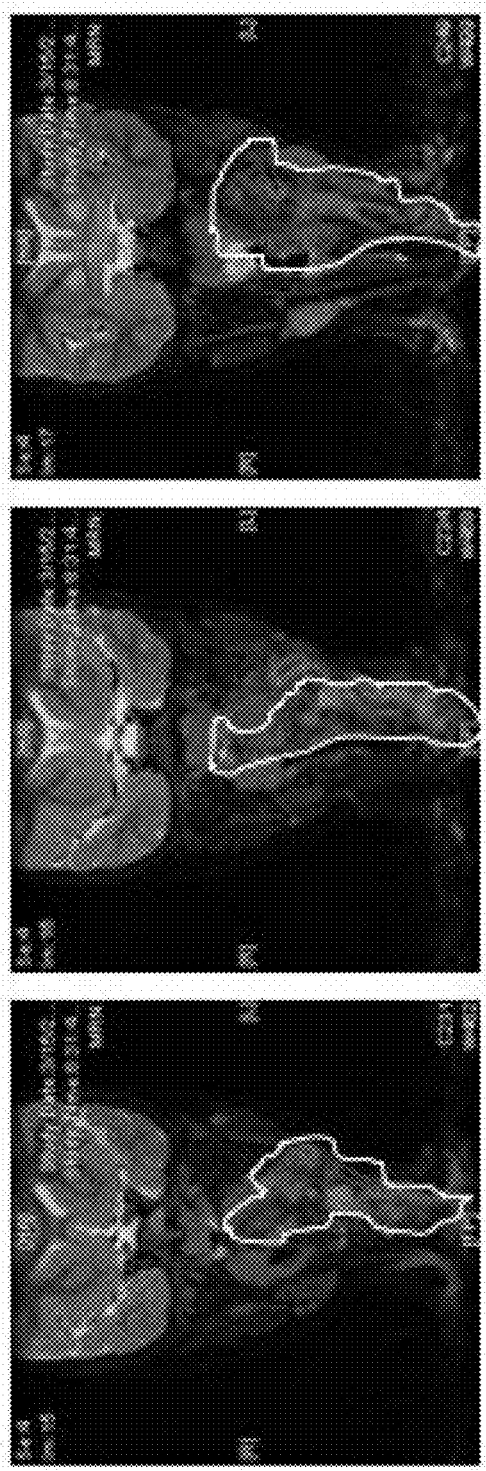
FIG. 13A. MRI images, head and neck.
Figure 13A:
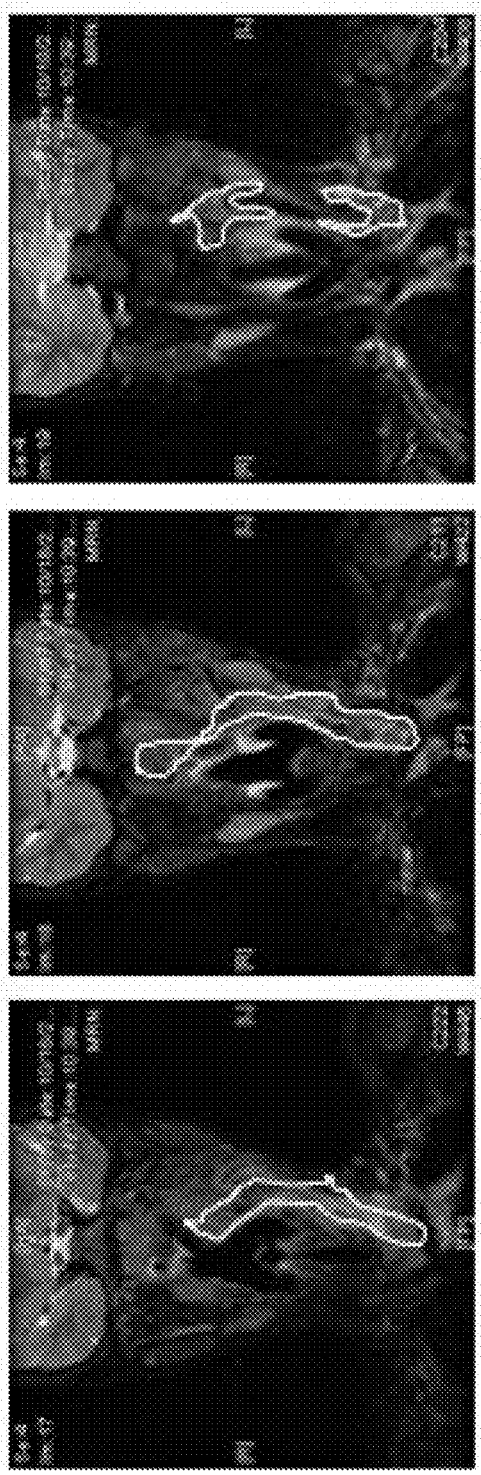

Referring now to FIG. 13A. The Panels in rows A, B are Coronal MRI T1 weighted STIR sequence images; pre-imatinib-mesylate (row A) and 6 months following treatment with imatinib mesylate, respectively (row B). These images demonstrate show evidence of a profound decrease in tumor size before and after treatment.

Figure 13B:
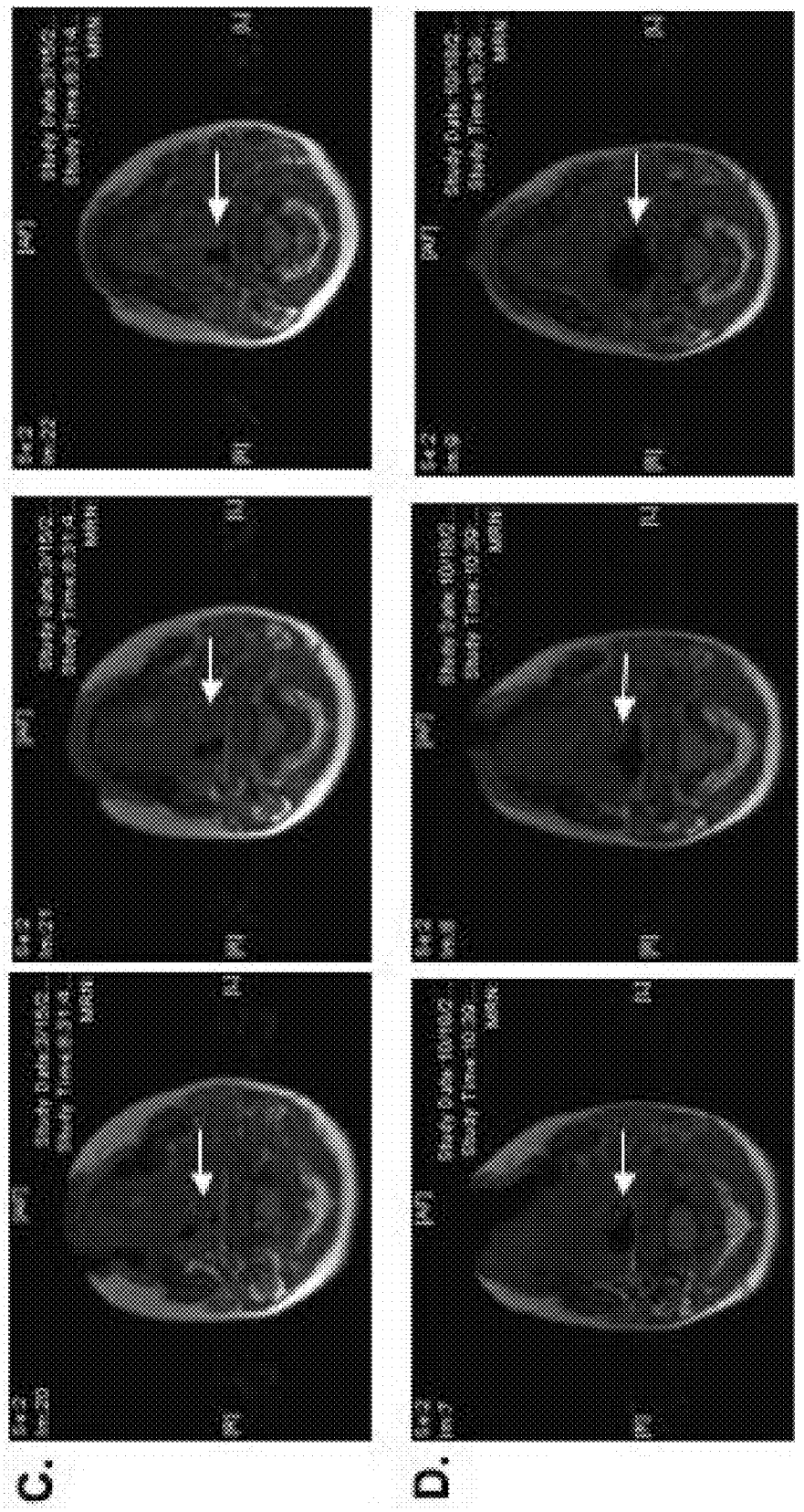
FIG. 13B. Panels C, D: Axial MRI T2 weighted sequence images; before and after 6 months of treatment with imatinib mesylate respectively.

Referring now to FIG. 13B, in both series of images, note the marked narrowing of the upper airway (arrow) with displacement to the right by tumor in the pre-imatinib mesylate images (row C) versus post-imatinib treatment (the images in row D). Images obtained after treatment with imatinib mesylate, show that there is a marked improvement with airway enlargement back toward the midline. The regions of the tumor in the respective images are indicated.

This is clear evidence a pharmaceutical intervention in a human being with the compound imatinib mesylate resulted in significant reduction in the size of a plexiform neurofibroma. Though reflecting the course of a single patient, this striking result is consistent with the preclinical studies in the murine model.

While exemplary embodiments incorporating the principles of various aspects and embodiments have been disclosed hereinabove, the present invention is not limited to the disclosed embodiments. Instead, this application is intended to cover any variations, uses, or adaptations of the information disclosed using the general principles disclosed herein. Further, this application is intended to cover such departures from the present disclosure as come within known or customary practice in the art to which this invention pertains and which fall within the limits of the appended claims and equivalents thereof.

What is claimed is:

1. A method of treating plexiform neurofibroma to a patient, comprising the steps of: providing at least one therapeutically effective dose of a compound according to Formula 1:

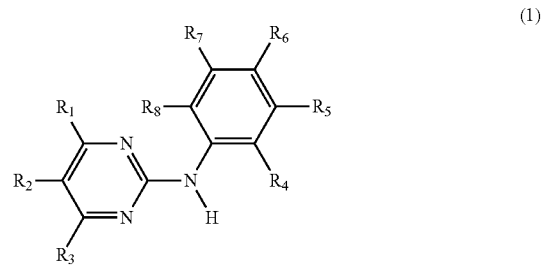

wherein, $R_1$ is 4-pyrazinyl; 1-methyl-1H-pyrrolyl; amino- or amino-lower alkyl-substituted phenyl, wherein the amino group in each case is free, alkylated or acylated; 1H-indolyl or 1H-imidazolyl bonded at a five-membered ring carbon atom; or unsubstituted or lower alkyl-substituted pyridyl bonded at a ring carbon atom and unsubstituted or substituted at the nitrogen atom by oxygen;

$R_2$ and $R_3$ are each independently of the other hydrogen or lower alkyl;

one or two of the radicals $R_4$, $R_5$, $R_6$, $R_7$ and $R_8$ are each nitro, fluoro-substituted lower alkoxy or a radical of formula II

 (II);

wherein, $R_9$ is hydrogen or lower alkyl,

X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms, or an aromatic, aromatic-aliphatic, cycloaliphatic, cycloaliphatic-aliphatic, heterocyclic or heterocyclic-aliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, pyrrolidinyl or by morpholinyl, or lower alkanoyl, trifluoromethyl, free, etherified or esterifed hydroxy, free, alkylated or acylated amino or free or esterified carboxy, or of a salt of such a compound having at least one salt-forming group.

2. The method according to claim 1, wherein the compound is a pharmaceutically acceptable salt of Formula 1.

3. The method according to claim 2, wherein the pharmaceutically acceptable salt of Formula 1 is a mesylate salt.

4. The method according to claim 1, further including the step of: diagnosing a patient with plexiform neurofibroma or a similar condition.

5. The method according to claim 1, further including the step of: identifying a patient at risk for developing plexiform neurofibroma or a similar condition.

6. The method according to claim 1, wherein the therapeutically effective dose of the compound according to Formula 1, is on the order of between about 200 mg to about 500 mg and the dose of the compound is administered to a patient at least once per day.

7. The method according to claim 1, wherein the therapeutically effective dose of the compound according to Formula 1, is on the order of between about 350 mg to about 450 mg and the dose of the compound is administered to a patient at least once per day.

8. The method according to claim 1, wherein the therapeutically effective dose of the compound according to Formula 1, is about 400 mg and the dose of the compound is administered to a patient twice per day.

* * * * *